United States Patent
Aslanidi et al.

(10) Patent No.: US 10,927,150 B2
(45) Date of Patent: Feb. 23, 2021

(54) RECOMBINANT AAV1, AAV5, AND AAV6 CAPSID MUTANTS AND USES THEREOF

(71) Applicant: University of Florida Research Foundation, Incorporated, Gainesville, FL (US)

(72) Inventors: George Vladimirovich Aslanidi, Austin, MN (US); Kim M. Van Vliet, Gainesville, FL (US); Mavis Agbandje-McKenna, Gainesville, FL (US); Arun Srivastava, Gainesville, FL (US)

(73) Assignee: University of Florida Research Foundation, Incorporated, Gainesville, FL (US)

( * ) Notice: Subject to any disclaimer, the term of this patent is extended or adjusted under 35 U.S.C. 154(b) by 0 days.

(21) Appl. No.: 16/565,191

(22) Filed: Sep. 9, 2019

(65) Prior Publication Data
US 2020/0010510 A1 Jan. 9, 2020

Related U.S. Application Data

(63) Continuation of application No. 15/548,728, filed as application No. PCT/US2016/016422 on Feb. 3, 2016, now abandoned.
(Continued)

(51) Int. Cl.
*C12N 7/00* (2006.01)
*C12N 15/00* (2006.01)
(Continued)

(52) U.S. Cl.
CPC ............ *C07K 14/005* (2013.01); *C12N 15/86* (2013.01); *C12N 15/861* (2013.01); *A61K 48/00* (2013.01);
(Continued)

(58) Field of Classification Search
None
See application file for complete search history.

(56) References Cited

U.S. PATENT DOCUMENTS 6,156,303 A 12/2000 Russell et al.
7,052,692 B1 5/2006 Srivastava et al.
(Continued)

FOREIGN PATENT DOCUMENTS

CA 2826273 A1 8/2012
CN 102159713 A 8/2011
(Continued)

OTHER PUBLICATIONS

McClements et al., "Gene therapy for retinal disease", Transl. Res 161(4): 1-21 (Year: 2013).*
(Continued)

*Primary Examiner* — M Franco G Salvoza
(74) *Attorney, Agent, or Firm* — Wolf, Greenfield & Sacks, P.C.

(57) ABSTRACT

Provided herein are modified recombinant adeno-associated virus (rAAV) capsid proteins, such as modified rAAV1, rAAV5, and rAAV6 capsid proteins, rAAV particles comprising such capsid proteins, nucleic acid molecules encoding such capsid proteins, as well as compositions, kits and methods of use thereof.

17 Claims, 8 Drawing Sheets

Specification includes a Sequence Listing.

Related U.S. Application Data

(60) Provisional application No. 62/111,319, filed on Feb. 3, 2015.

(51) Int. Cl.
*C07K 14/005* (2006.01)
*C12N 15/86* (2006.01)
*C12N 15/861* (2006.01)
*A61K 48/00* (2006.01)

(52) U.S. Cl.
CPC .............. *C12N 2750/14122* (2013.01); *C12N 2750/14143* (2013.01)

(56) References Cited

U.S. PATENT DOCUMENTS

| | | |
|---|---|---|
| 8,445,267 B2 | 5/2013 | Zhong et al. |
| 8,802,440 B2 | 8/2014 | Zhong et al. |
| 9,157,098 B2 | 10/2015 | Zhong et al. |
| 9,611,302 B2 | 4/2017 | Srivastava et al. |
| 9,725,485 B2 | 8/2017 | Srivastava et al. |
| 9,775,918 B2 | 10/2017 | Zhong et al. |
| 9,920,097 B2 | 3/2018 | Zhong et al. |
| 10,011,640 B2 | 7/2018 | Srivastava et al. |
| 10,294,281 B2 | 5/2019 | Srivastava et al. |
| 10,426,844 B2 | 10/2019 | Agbandje-McKenna et al. |
| 2003/0138772 A1 | 7/2003 | Gao et al. |
| 2003/0219733 A1 | 11/2003 | Clark et al. |
| 2006/0292117 A1 | 12/2006 | Loiler et al. |
| 2010/0104561 A1 | 4/2010 | Zhong et al. |
| 2013/0203841 A1 | 8/2013 | Zhong et al. |
| 2013/0216501 A1 | 8/2013 | Zhong et al. |
| 2013/0224836 A1 | 8/2013 | Muramatsu |
| 2013/0310443 A1 | 11/2013 | Srivastava et al. |
| 2014/0050701 A1 | 2/2014 | Zhong et al. |
| 2014/0341852 A1 | 11/2014 | Srivastava et al. |
| 2015/0133530 A1 | 5/2015 | Srivastava et al. |
| 2016/0106865 A1 | 4/2016 | Zhong et al. |
| 2016/0333372 A1 | 11/2016 | Srivastava et al. |
| 2016/0361439 A1 | 12/2016 | Agbandje-McKenna et al. |
| 2016/0369299 A1 | 12/2016 | Boye et al. |
| 2017/0275337 A1 | 9/2017 | Srivastava et al. |
| 2018/0030096 A1 | 2/2018 | Aslanidi et al. |
| 2018/0036428 A1 | 2/2018 | Zhong et al. |
| 2018/0105559 A1 | 4/2018 | Zhong et al. |
| 2018/0135074 A1 | 5/2018 | Srivastava et al. |
| 2018/0223312 A1 | 8/2018 | Srivastava et al. |
| 2018/0244727 A1 | 8/2018 | Zhong et al. |
| 2019/0000943 A1 | 1/2019 | Aslanidi |
| 2019/0016759 A1 | 1/2019 | Srivastava et al. |
| 2019/0127424 A1 | 5/2019 | Srivastava et al. |
| 2019/0284244 A1 | 9/2019 | Srivastava et al. |

FOREIGN PATENT DOCUMENTS

| | | |
|---|---|---|
| CN | 102994549 A | 3/2013 |
| CN | 103060331 A | 4/2013 |
| CN | 104470945 A | 3/2015 |
| EP | 1 310 571 A2 | 5/2003 |
| EP | 1 486 567 A1 | 12/2004 |
| EP | 2 660 325 A2 | 11/2013 |
| WO | WO 03/006616 A2 | 1/2003 |
| WO | WO 03/052052 A2 | 6/2003 |
| WO | WO 2004/027019 A2 | 4/2004 |
| WO | WO 2004/111248 A2 | 12/2004 |
| WO | WO 2005/033321 A2 | 4/2005 |
| WO | WO 2006/110689 A2 | 10/2006 |
| WO | WO 2006/119150 A2 | 11/2006 |
| WO | WO 2008/124724 A1 | 10/2008 |
| WO | WO 2008/145400 A2 | 12/2008 |
| WO | WO 2011/133890 A1 | 10/2011 |
| WO | WO 2012/057363 A2 | 5/2012 |
| WO | WO 2013/158879 A1 | 10/2013 |
| WO | WO 2013/173512 A1 | 11/2013 |
| WO | WO 2014/193716 A1 | 12/2014 |

OTHER PUBLICATIONS

EP Examination Report dated Jan. 27, 2011, issued in EP 08733161.7-2405 (3 pages).
Examination Report dated Oct. 22, 2013, issued in CIPO 2,720,097 (2 pages).
Extended European Search Report for Application No. EP 118202680.7 dated Jul. 31, 2019.
Extended European Search Report for Application No. EP 18201865.5 dated Feb. 27, 2019.
International Preliminary Report on Patentability for Application No. PCT/US2008/059647 dated Oct. 22, 2019.
International Preliminary Report on Patentability for Application No. PCT/US2013/041234 dated Nov. 27, 2014.
International Preliminary Report on Patentability for Application No. PCT/US2014/039015 dated Dec. 3, 2015.
International Preliminary Report on Patentability for Application No. PCT/US2016/016422 dated Aug. 17, 2017.
International Search Report and Written Opinion for Application No. PCT/US2008/059647 dated Sep. 10, 2008.
International Search Report and Written Opinion for Application No. PCT/US2013/041234 dated Feb. 13, 2014.
International Search Report and Written Opinion for Application No. PCT/US2014/039015 dated Nov. 24, 2014.
International Search Report and Written Opinion for Application No. PCT/US2016/016422 dated May 5, 2016.
Partial European Search Report for Application EP 18202680.7 dated Apr. 29, 2019.
Response to EP Examination Report dated Jul. 25, 2011, issued in EP 08733161.7-2405 (8 pages).
[No Author Listed] Database UniProt KB, Accession B4Y866 (B4Y886_9VIRU9), Integrated into UniProt KB/TrEMBL Sep. 23, 2008, Last modified Jul. 31 2019. 4 pages.
[No Author Listed] Database UniProt KB, Accession Q808W7 (Q808W7-9VIRU), Integrated into UniProt KB/TrEMBL Jun. 1, 2003, Last modified Jul. 31, 2019. 4 pages.
Aslanidi et al, High-efficiency transduction of human monocyte-derived dendritic cells by capsid-modified recombinant AAV2 vectors. Vaccine. Jun. 6, 2012;30(26):3908-17. doi: 10.1016/j.vaccine.2012.03.079. Epub Apr. 10, 2012.
Aslanidi et al, Optimization of the capsid of recombinant adeno-associated virus 2 (AAV2) vectors: the final threshold? PLoS One. 2013;8(3):e59142. doi: 10.1371/journal.pone.0059142. Epub Mar. 19, 2013.
Aslanidi et al., Abstract 333: High-Efficiency Transduction of Primary Human Monocyte-Derived Dendritic Cells by Recombinant AAV6 Vectors Containing Mutations in Surface-Exposed Serine and Threonine Residues. Molecular Therapy. May 2013;21(S1):S129.
Aslanidi et al., Abstract 334: Optimization of the capsid of recombinant adeno-associated virus 2 (AAV2) vectors: the final threshold? Molecular Therapy. May 2013;21(S1):S129.
Aslanidi et al., Abstract C240: Modification on the capsid of recombinant adeno-associated virus vectors (rAAV) leads to high-efficiency transduction of human monocyte-derived dendritic cells (moDCs). Mol Cancer Ther. Nov. 2011. 10(11): Abstract C240. 3 Pages.
Bantel-Schaal et al., Human adeno-associated virus type 5 is only distantly related to other known primate helper-dependent parvoviruses. J Virol. Feb. 1999;73(2):939-47.
Cheng et al, Development of optimized AAV3 serotype vectors: mechanism of high-efficiency transduction of human liver cancer cells. Gene Ther. Apr. 2012;19(4):375-84. doi: 10.1038/gt.2011.105. Epub Jul. 21, 2011.
Chiorini et al., Capsid Protein [Adeno-associated virus-5] Genbank Accession No. YP-068409 Dec. 8, 2008. 2 pages.
Dalkara et al., Enhanced gene delivery to the neonatal retina through systemic administration of tyrosine-mutated AAV9. Gene Ther. Feb. 2012;19(2):176-81. doi: 10.1038/gt.2011.163. Epub Oct. 20, 2011.
De Oliveira et al., Herpes simplex virus type 1/adeno-associated virus hybrid vectors. Open Virol J. Jun. 18, 2010;4:109-22. doi: 10.2174/1874357901004030109.

(56) References Cited

OTHER PUBLICATIONS

Doroudchi et al., Virally delivered channelrhodopsin-2 safely and effectively restores visual function in multiple mouse models of blindness. Mol Ther. Jul. 2011;19(7):1220-9. doi: 10.1038/mt.2011. 69. Epub Apr. 19, 2011.
Gabriel et al., Bioengineering of AAV2 capsid at specific serine, threonine, or lysine residues improves its transduction efficiency in vitro and in vivo. Hum Gene Ther Methods. Apr. 2013;24(2):80-93. doi: 10.1089/hgtb.2012.194. Epub Mar. 15, 2013.
Gabriel et al., Targeted Mutagenesis of Ubiquitin-Binding Lysine Residues on the Adeno-Associated Virus (AAV)2 Capsid Improves Its Transduction Efficiency. Mol Ther. 2012;20(Supp 1):S146.
Gao et al., Clades of Adeno-associated viruses are widely disseminated in human tissues. J Virol. Jun. 2004;78(12):6381-8.
Gao et al., Novel adeno-associated viruses from rhesus monkeys as vectors for human gene therapy. Proc Natl Acad Sci U S A. Sep. 3, 2002;99(18):11854-9. Epub Aug. 21, 2002.
Horowitz et al., Tyrosine cross-linking reveals interfacial dynamics in adeno-associated viral capsids during infection. ACS Chemical Biology, pubs.acs.org/acschemicalbiology, ACS Publications, ACS Chem Biol. Jun. 15, 2012;7(6):1059-66. doi: 10.1021/cb3000265. Epub Apr. 6, 2012.
Jayandharan et al., Activation of the NF-kappaB pathway by adeno-associated virus (AAV) vectors and its implications in immune response and gene therapy. Proc Natl Acad Sci U S A. Mar. 1, 2011;108(9):3743-8. doi: 10.1073/pnas.1012753108. Epub Feb. 14, 2011.
Kauss et al., Enhanced long-term transduction and multilineage engraftment of human hematopoietic stem cells transduced with tyrosine-modified recombinant adeno-associated virus serotype 2. Hum Gene Ther. Sep. 2010;21(9):1129-36. doi: 10.1089/hum.2010. 016.
Kay et al., Targeting photoreceptors via intravitreal delivery using novel, capsid-mutated AAV vectors. PLoS One. Apr. 26, 2013;8(4):e62097. doi: 10.1371/journal.pone.0062097. Print 2013.
Kern et al., Identification of a heparin-binding motif on adeno-associated virus type 2 capsids. J Virol. Oct. 2003;77(20):11072-81.
Ku et al., Gene therapy using self-complementary Y733F capsid mutant AAV2/8 restores vision in a model of early onset Leber congenital amaurosis.Hum Mol Genet. Dec. 1, 2011;20(23):4569-81. doi: 10.1093/hmg/ddr391. Epub Aug. 31, 2011.
Le Meur et al., Restoration of vision in RPE65-deficient Briard dogs using an AAV serotype 4 vector that specifically targets the retinal pigmented epithelium. Gene Therapy 14(4):292-303 (Feb. 2007), 12 pages.
Li et al., Site-Directed Mutagenesis of Surface-Exposed Lysine Residues Leads To Improved Transduction By Recombinant Aav2 and Aav8 Vectors in Murine Hepatocytes in Vivo. Mol Ther. 2013;21(Supp 1):S208-9.
Li et al., Site-Directed Mutagenesis of Surface-Exposed Lysine Residues Leads to Improved Transduction by AAV2, But Not AAV8, Vectors in Murine Hepatocytes In Vivo. Hum Gene Ther Methods. Dec. 2015;26(6):211-20. doi: 10.1089/hgtb.2015.115. Epub Oct. 27, 2015.
Li et al., The fecal viral flora of California sea lions. J Virol. Oct. 2011;85(19):9909-17. doi: 10.1128/JVI.05026-11. Epub Jul. 27, 2011.
Ling et al, Selective in vivo targeting of human liver tumors by optimized AAV3 vectors in a murine xenograft model. Hum Gene Ther. Dec. 2014;25(12):1023-34. doi: 10.1089/hum.2014.099.
Lochrie et al., Mutations on the External Surfaces of Adeno-Associated Virus Type 2 Capsids That Affect Transduction and Neutralization. Journal of Virology 80(2):821-834 (Jan. 2006), 14 pages.
Locke et al., Transduction of Human Adipose-Derived Mesenchymal Stem Cells by Recombinant Adeno-Associated Virus Vectors. COPYRGT. Mary Ann Liebert, Inc., DOI: 10.1089/ten.tec.2011. 0153, Tissue Engineering: Part C; vol. 17, No. 9,2011, pp. 949-959.
Markusic et al., High-Efficiency Transduction and Correction of Murine Hemophelia B Using AAV2 Vectors Devoid of Multiple Surface-Exposed Tyrosines. Molecular Therapy (Dec. 2010), vol. 18, No. 12, pp. 2048-2056.
Mori et al., Two novel adeno-associated viruses from cynomolgus monkey: pseudotyping characterization of capsid protein. Virology. Dec. 20, 2004;330(2):375-83.
Opie et al., Identification of amino acid residues in the capsid proteins of adeno-associated virus type 2 that contribute to heparan sulfate proteoglycan binding. J Virol. Jun. 2003;77(12):6995-7006.
Pandya et al., Rationally designed capsid and transgene cassette of AAV6 vectors for dendritic cell-based cancer immunotherapy. Immunol Cell Biol. Feb. 2014;92(2):116-23. doi: 10.1038/icb.2013.74. Epub Nov. 12, 2013.
Pang et al., Long-Term Retinal Function and Structure Rescue Using Capsid Mutant AAV8 Vector in the rd10 Mouse, a Model or Recessive Retinitis Pigmentosa.COPYRGT. The American Society of Gene & Cell Therapy, Molecular Therapy, pp. 1-9,2010.
Petrs-Silva et al., High-Efficiency Transduction of the Mouse Retina by Tyrosine-Mutant AAV Serotype Vectors.COPYRGT. The American Society of Gene & Cell Therapy, www.moleculartherapy.org, Molecular Therapy, vol. 17, No. 3, pp. 463-471,Mar. 2009.
Petrs-Silva et al., Novel Properties of Tyrosine-Mutant AAV2 Vectors in the Mouse Retina.COPYRGT. The American Society of Gene & Cell Therapy, www.moleculartherapy.org, Molecular Therapy, vol. 19, No. 2, pp. 293-301, Feb. 2011.
Qi et al., Comparison of Transduction Efficiency of Tyrosine-Mutant AAV Serotype Vectors in Kidney.COPYRGT. 2012 The Authors Clinical and Experimental Pharmacology and Physiology, .COPYRGT. 2012 Wiley Publishing Asia Pty Ltd., doi:10.1111/1440-1681.12037, 8 pages.
Qiao et al., Adeno-Associated Virus Serotype 6 Capsid Tyrosine-to-Phenylalanine Mutations Improve Gene Transfer to Skeletal Muscle. Human Gene Therapy 21:1343-1348 (Oct. 2010), .COPYRGT. Mary Ann Liebert, Inc., doi:10.1089/hum.2010.003, pp. 1343-1348.
Qiao et al., Single Tyrosine Mutation in AAV8 and AAV9 Capsids Is Insufficient to Enhance Gene Delivery to Skeletal Muscle and Heart. Human Gene Therapy Methods: Part B 23:29-37 (Feb. 2012), .COPYRGT. Mary Ann Liebert, Inc., doi:10.1089/hgtb.2011. 229, pp. 29-37.
Radivojac et al., Identification, analysis, and prediction of protein ubiquitination sites. Proteins. Feb. 1, 2010;78(2):365-80. Author manuscript.
Rakoczy et al., Development of Gene Therapy-Based Strategies for the Treatment of Eye Diseases. Drug Development Research. 1999;46:277-285.
Ruan et al., Development of an Anti-Angiogenic Therapeutic Model Combining scAAV2-delivered siRNAs and Noninvasive Photoacoustic Imaging of Tumor Vasculature Development. Cancer Lett. (2012), http://dx.doi.org/10.1016/j.canlet.2012.11.016,Dec. 4, 2012, 10 pages.
Rutledge et al., Infectious clones and vectors derived from adeno-associated virus (AAV) serotypes other than AAV type 2. J Virol. Jan. 1998;72(1):309-19.
Ryals et al., Quantifying Transduction Efficiencies of Unmodified and Tyrosine Capsid Mutant AAV Vectors in Vitro Using Two Ocular Cell Lines. Molecular Vision 2011; 17:1090-1102 (http://www.molvis.org/molvis/v17/a124), Apr. 29, 2011,pp. 1090-1102.
Schaffer et al., GenBank Submission: ADW24578. Apr. 7, 2005. 2 pages.
Shin et al., A Simplified Immune Suppression Scheme Leads to Persistent Micro-Dystrophin Expression in Duchenne Muscular Dystrophy Dogs. Human Gene Therapy 23:202-209 (Feb. 2012), .COPYRGT. Mary Ann Libert, Inc., doi:10.1089/hum. 2011,147, pp. 202-209.
Song et al., High-efficiency transduction of primary human hematopoietic stem cells and erythroid lineage-restricted expression by optimized AAV6 serotype vectors in vitro and in a murine xenograft model in vivo. PLoS One. 2013;8(3):e58757. doi: 10.1371/journal.pone.0058757. Epub Mar. 14, 2013.
Song et al., Optimizing the transduction efficiency of capsid-modified AAV6 serotype vectors in primary human hematopoietic stem cells in vitro and in a xenograft mouse model in vivo. Cytotherapy. 2013;15:986-98.

(56) References Cited

OTHER PUBLICATIONS

Ussher et al., Optimized Transduction of Human Monocyte-Derived Dendritic Cells by Recombinant Adeno-Associated Virus Serotype 6. Human Gene Therapy 21:1675-1686 (Dec. 2010), .COPYRGT. Mary Ann Liebert, Inc., doi: 10.1089/hum.2010.078,pp. 1675-1686.

Vandenberghe et al., Naturally occurring singleton residues in AAV capsid impact performance and illustrate structural constraints. Submitted 2007. EMBL/GenBank/DDBJ databases. Accession number: B4Y882_9VIRU.

Wang et al., Limitations of encapsidation of recombinant self-complementary adeno-associated viral genomes in different serotype capsids and their quantitation. Hum Gene Ther Methods. Aug. 2012;23(4):225-33. doi: 10.1089/hgtb.2012.090.

Yan et al. Ubiquitination of both Adeno-Associated Virus Type 2 and 5 Capsid Proteins Affects the Transduction Efficiency of Recombinant Vectors, Journal of Virology 76(5):2043-2053 (Mar. 2002), 11 pages.

Zhong et al., A Dual Role of EGFR Protein Tyrosine Kinase Signaling in Ubiquitination of AAV2 Capsids and Viral Second-strand DNA Synthesis. The American Society of Gene Therapy, Molecular Therapy 15(7):1323-1330 (Jul. 2007), 8 pages.

Zhong et al., Evaluation of Primitive Murine Hematopoietic Stem and Progenitor Cell Transduction In Vitro and In Vivo by Recombinant Adeno-Associated Virus Vector Serotypes 1 Through 5. Human Gene Therapy 17(3):321-333 (Mar. 2006), 13 pages.

Zhong et al., Next generation of adeno-associated virus 2 vectors: Point mutations in tyrosines lead to high-efficiency transduction at lower doses. Proc Natl Acad Sci U S A. Jun. 3, 2008;105(22):7827-32. doi: 10.1073/pnas.0802866105. Epub May 29, 2008. Erratum in Proc Natl Acad Sci U S A. Aug. 5, 2008;105(31):11032.

Glushakova et al., 459. High-Efficiency Transduction of Human Hepatoblastoma and Hepatocellular Carcinoma Cells by the Wild-Type and the Tyrosine-Mutant AAV3 Serotype Vectors. Mol Ther. 2009;17(S1):S179.

Jayandharan et al., 372. Human Hematopoietic Stem Cell Transduction by AAV Vectors: Identification of AAV6 as the Most Efficient Serotype, and Further Augmentation in Transduction Efficiency with Point-Mutations at Tyrosine Residues 705 and 731in the Viral Capsid. Mol Ther. 2009;17(S1):S145-6.

Kauss et al., 457. Tyrosine-Modified rAAV2 Vectors Display Enhanced Transduction of Human Hematopoietic Stem Cells. Mol Ther. 2009;17(S1):S178.

Markusic et al., 765. Novel AAV2 Tyrosine Mutant Capsids Provide Long-Term Therapeutic Factor IX Expression in a Difficult To Tolerize Murine Hemophilia Model. Mol Ther. 2009;17(S1):S292.

Qiao et al., 451. Comparison of Transduction Efficiency of Tyrosine-Mutant AAV Vectors in Muscle. Mol Ther. 2009;17(S1):S175-6.

Zhang et al., 453. Novel Tyrosine Mutant Vectors Expand the Utilities of AAV-Mediated Muscle Gene Therapy. Mol Ther. 2009;17(S1):S176-7.

Zhong et al., 371. High-Efficiency Transduction of Human Cells In Vitro and Murine Hepatocytes In Vivo at Further Reduced Doses of AAV2 Vectors Containing Multiple Mutations in Surface-Exposed Tyrosine Residues in the Viral Capsid. Mol Ther. May 2009;17(S1):S145.

Zhong et al., 90. Critical Requirement of a Cellular Chaperone Protein, FKBP52, for Intracellular Trafficking and Nuclear Transport of Tyrosine-Mutant AAV2 Vectors for High-Efficiency Transduction of Murine Embryo Fibroblasts. Mol Ther. May 2009;17(S1):S36-7.

U.S. Appl. No. 15/680,668, filed Aug. 18, 2017, Zhong et al.
U.S. Appl. No. 15/672,265, filed Aug. 8, 2017, Zhong et al.
U.S. Appl. No. 16/283,705, filed Feb. 22, 2019, Srivastava et al.
U.S. Appl. No. 15/824,023, filed Nov. 28, 2017, Srivastava et al.
U.S. Appl. No. 15/896,390, filed Feb. 14, 2018, Zhong et al.
U.S. Appl. No. 15/987,993, filed May 24, 2018, Srivastava et al.
U.S. Appl. No. 16/179,818, filed Nov. 2, 2018, Srivastava et al.
U.S. Appl. No. 15/548,728, filed Aug. 3, 2017, Aslanidi et al.
CA 2,720,097, Oct. 22, 2013, Examination Report.
EP 08733161.7, Jan. 27, 2011, EP Examination Report.
EP 08733161.7, Jul. 25, 2011, Response to EP Examination Report.
EP 18201865.5, Feb. 27, 2019, Extended European Search Report.
PCT/US2008/059647, Sep. 10, 2008, International Search Report and Written Opinion.
PCT/US2008/059647, Oct. 22, 2009, International Preliminary Report on Patentability.
PCT/US2013/041234, Feb. 13, 2014, International Search Report and Written Opinion.
PCT/US2013/041234, Nov. 27, 2014, International Preliminary Report on Patentability.
EP 18202680.7, Apr. 29, 2019, Partial European Search Report.
EP 18202680.7, Jul. 31, 2019, Extended European Search Report.
PCT/US2014/039015, Nov. 24, 2014, International Search Report and Written Opinion.
PCT/US2014/039015, Dec. 3, 2015, International Preliminary Report on Patentability.
PCT/US2016/016422, May 5, 2016, International Search Report and Written Opinion.
PCT/US2016/016422, Aug. 17, 2017, International Preliminary Report on Patentability.

* cited by examiner

US 10,927,150 B2

RECOMBINANT AAV1, AAV5, AND AAV6 CAPSID MUTANTS AND USES THEREOF

RELATED APPLICATIONS

This application is a continuation of U.S. application Ser. No. 15/548,728, filed Aug. 3, 2017 which is a national stage filing under 35 U.S.C § 371 of PCT International Application PCT/US2016/016422, filed Feb. 3, 2016, entitled "RECOMBINANT AAV1, AAV5, AND AAV6 CAPSID MUTANTS AND USES THEREOF," which claims priority under 35 U.S.C. § 119(e) to U.S. provisional application No. 62/111,319, filed Feb. 3, 2015, the contents each of which are incorporated herein by reference in their entireties.

GOVERNMENT SUPPORT

This invention was made with government support under grant numbers HL097088 and EB-015684 awarded by the National Institutes of Health. The government has certain rights in the invention.

BACKGROUND OF INVENTION

Gene therapy using recombinant adeno-associated virus (rAAV) vectors has advanced significantly in the last decade. However, the transduction efficiency of rAAV vectors varies widely between different cells and tissues in vitro and in vivo.

SUMMARY OF THE INVENTION

As described herein, rAAV1, rAAV5, and rAAV6 capsid mutant-containing viral particles were shown to transduce different tissues and cells (e.g., muscle, retina, airway epithelia, hematopoietic stem cells, dendritic cells, monocytes, airway epithelial cells, and microglial cells) with high efficiency, when compared to rAAV particles comprising wild-type capsid proteins.

Accordingly, the present disclosure provides AAV capsid proteins comprising modifications of a combination of one or more of the surface-exposed residues. Also provided are rAAV viral particles that comprise the modified AAV capsid proteins, as well as nucleic acid molecules and rAAV vectors encoding the modified AAV capsid proteins. Also disclosed herein are methods utilizing such proteins, viral particles, nucleic acid molecules and rAAV vectors.

In some embodiments, the present disclosure provides a nucleic acid molecule comprising a nucleotide sequence encoding an AAV capsid protein (e.g., an AAV1, AAV5, or AAV6 capsid protein), wherein the VP3 region of the capsid protein comprises modifications (e.g., replacement of a tyrosine residue with a non-tyrosine residue and/or a threonine residue with a non-threonine residue) at positions corresponding to:
one or more of or each of Y705, Y731, and T492 of a wild-type AAV1 capsid protein (e.g., SEQ ID NO: 1),
one or more of or each of Y436, Y693, and Y719 of a wild-type AAV5 capsid protein (e.g., SEQ ID NO: 2), or
one or more of or each of Y705, Y731, and T492 of a wild-type AAV6 capsid protein (e.g., SEQ ID NO: 3).

In some embodiments, the nucleotide sequence encodes an AAV capsid protein (e.g., an AAV1, AAV5, or AAV6 capsid protein) comprising Y to F (tyrosine to phenylalanine) modifications or T to V (threonine to valine) modifications in the VP3 region of the capsid at positions corresponding to:
one or more of or each of Y705F, Y731F, and T492V of a wild-type AAV1 capsid protein (e.g., SEQ ID NO: 1),
one or more of or each of Y436F, Y693F, and Y719F of a wild-type AAV5 capsid protein (e.g., SEQ ID NO: 2), or
one or more of or each of Y705F, Y731F, and T492V of a wild-type AAV6 capsid protein (e.g., SEQ ID NO: 3).

In some embodiments, the present disclosure provides an AAV capsid protein (e.g., an AAV1, AAV5, or AAV6 capsid protein), wherein a VP3 region of the capsid protein comprises modifications (e.g., replacement of a tyrosine residue with a non-tyrosine residue and/or a threonine residue with a non-threonine residue) at positions corresponding to:
one or more of or each of Y705, Y731, and T492 of a wild-type AAV1 capsid protein (e.g., SEQ ID NO: 1),
one or more of or each of Y436, Y693, and Y719 of a wild-type AAV5 capsid protein (e.g., SEQ ID NO: 2), or
one or more of or each of Y705, Y731, and T492 of a wild-type AAV6 capsid protein (e.g., SEQ ID NO: 3).

In some embodiments, the AAV capsid protein (e.g., an AAV1, AAV5, or AAV6 capsid protein) comprises Y to F (tyrosine to phenylalanine) modifications or T to V (threonine to valine) modifications in the VP3 region of the capsid protein at positions corresponding to:
one or more of or each of Y705F, Y731F, and T492V of a wild-type AAV1 capsid protein (e.g., SEQ ID NO: 1),
one or more of or each of Y436F, Y693F, and Y719F of a wild-type AAV5 capsid protein (e.g., SEQ ID NO: 2), or
one or more of or each of Y705F, Y731F, and T492V of a wild-type AAV6 capsid protein (e.g., SEQ ID NO: 3).

In some embodiments, the present disclosure provides an rAAV particle comprising an AAV capsid protein (e.g., an AAV1, AAV5, or AAV6 capsid protein), wherein the VP3 region of the capsid protein comprises modifications (e.g., replacement of a tyrosine residue with a non-tyrosine residue and/or a threonine residue with a non-threonine residue) at positions corresponding to:
one or more of or each of Y705, Y731, and T492 of a wild-type AAV1 capsid protein (e.g., SEQ ID NO: 1),
one or more of or each of Y436, Y693, and Y719 of a wild-type AAV5 capsid protein (e.g., SEQ ID NO: 2), or
one or more of or each of Y705, Y731, and T492 of a wild-type AAV6 capsid protein (e.g., SEQ ID NO: 3).

In some embodiments, the rAAV particle comprises an AAV capsid protein (e.g., an AAV1, AAV5, or AAV6 capsid protein) comprising Y to F modifications or T to V modifications in the VP3 region at positions corresponding to:
one or more of or each of Y705F, Y731F, and T492V of a wild-type AAV1 capsid protein (e.g., SEQ ID NO: 1),
one or more of or each of Y436F, Y693F, and Y719F of a wild-type AAV5 capsid protein (e.g., SEQ ID NO: 2), or
one or more of or each of Y705F, Y731F, and T492V of a wild-type AAV6 capsid protein (e.g., SEQ ID NO: 3).

In related embodiments, the disclosure provides methods for using the viral particles, nucleic acids, vectors, proteins and compositions disclosed herein, and further provides processes for the transduction of one or more cells, one or more tissues, and/or one or more organs of interest, and particularly those of a mammalian animal using the disclosed viral particles. In an overall and general sense, such methods generally include at least the step of contacting a suitable host cell of interest with at least a first composition that comprises, consists essentially of, or alternatively consists of, an effective amount of a rAAV viral particle described herein, in an amount and for a time sufficient to transform at least a first cell or a first population of cells with a nucleic acid segment contained within the particle. In some embodiments, the viral particles of the present disclosure are preferably useful as vectors for introducing one or more nucleic acid segments to a selected host cell of interest. Preferably the host cell is a mammalian host cell, with human host cells being particularly preferred as targets for the rAAV particles described herein. In certain embodiments, such rAAV particles will comprise one or more isolated nucleic acid segments (e.g., DNA segments) encoding a selected therapeutic and/or diagnostic agent, including, for example one or more polynucleotides comprising one or more genes of interest or other therapeutic agent(s) that are capable of being expressed in a mammalian host cell that has been transformed by one or more of the rAAV viral particles described herein. Exemplary therapeutic agents include a polypeptide, a peptide, an antibody, an antigen binding fragment, a ribozyme, a peptide nucleic acid, a siRNA, an RNAi, an antisense oligonucleotide and an antisense polynucleotide.

In some embodiments, a method is provided, comprising: contacting a host cell (e.g., a muscle cell) with an rAAV particle comprising an AAV1 capsid protein, wherein the AAV1 capsid protein comprises modifications (e.g., replacement of a tyrosine residue with a non-tyrosine residue and/or a threonine residue with a non-threonine residue) in a VP3 region of the capsid protein at positions corresponding to Y705, Y731, and T492 of a wild-type AAV1 (e.g., SEQ ID NO: 1). In some embodiments, the AAV1 capsid protein comprises Y to F (tyrosine to phenylalanine) modifications or T to V (threonine to valine) modifications in the VP3 region of the capsid protein at positions corresponding to Y705F, Y731F, and T492V of a wild-type AAV1 capsid protein (e.g., SEQ ID NO: 1). The contacting may be in vitro (e.g., by administering to a cell in a dish or well) or in vivo (e.g., by administering the rAAV particle, e.g., as a composition comprising the rAAV particle, to a subject).

In some embodiments, a method is provided, comprising: contacting a host cell (e.g., a retinal or airway epithelial cell) with an rAAV particle comprising an AAV5 capsid protein, wherein the AAV5 capsid protein comprises modifications (e.g., replacement of a tyrosine residue with a non-tyrosine residue and/or a threonine residue with a non-threonine residue) in a VP3 region of the capsid protein at positions corresponding to Y436, Y693, and Y719 of a wild-type AAV5 capsid protein (e.g., SEQ ID NO: 2). In some embodiments, the AAV5 capsid protein comprises Y to F (tyrosine to phenylalanine) modifications in the VP3 region of the capsid protein at positions corresponding to Y436F, Y693F, and Y719F of a wild-type AAV5 capsid protein (e.g., SEQ ID NO: 2). The contacting may be in vitro (e.g., by administering to a cell in a dish or well) or in vivo (e.g., by administering the rAAV particle, e.g., as a composition comprising the rAAV particle, to a subject).

In some embodiments, a method is provided, comprising: contacting a host cell (e.g., a hematopoietic stem cell, a dendritic cell, a monocyte, airway an epithelial cell, a muscle cell, a liver cell, a pancreas cell or a microglial cell) with an rAAV particle comprising an AAV6 capsid protein, wherein the AAV6 capsid protein comprises modifications (e.g., replacement of a tyrosine residue with a non-tyrosine residue and/or a threonine residue with a non-threonine residue) in a VP3 region of the capsid protein at positions corresponding to Y705, Y731, and T492 of a wild-type AAV6 capsid protein (e.g., SEQ ID NO: 3). In some embodiments, the VP3 region of the AAV6 capsid protein comprises Y to F (tyrosine to phenylalanine) modifications or T to V (threonine to valine) modifications at positions corresponding to Y705F, Y731F, and T492V of a wild-type AAV6 capsid protein (e.g., SEQ ID NO: 3). The contacting may be in vitro (e.g., by administering the rAAV particle to a cell in a dish or well) or in vivo (e.g., by administering the rAAV particle, e.g., as a composition comprising the rAAV particle, to a subject).

In another aspect, the disclosure further provides compositions comprising rAAV particles, and pharmaceutical formulations thereof, useful in methods for delivering genetic material encoding one or more beneficial or therapeutic product(s) to mammalian cells and tissues. In particular, the compositions and methods of the disclosure provide a significant advancement in the art through their use in the treatment, prevention, and/or amelioration of symptoms of one or more mammalian diseases. It is contemplated that human gene therapy will particularly benefit from the present teachings by providing new and improved rAAV particles for use in the treatment of a number of diverse diseases, disorders, and dysfunctions.

In another aspect, the disclosure concerns a rAAV particle as described herein comprising a rAAV nucleic acid vector that encodes one or more mammalian therapeutic agents for the prevention, treatment, and/or amelioration of one or more disorders in the mammal into which the vector construct is delivered. In particular, the disclosure provides rAAV particles comprising rAAV-based nucleic acid expression constructs that encode one or more mammalian therapeutic agent(s) (including, but not limited to, for example, protein(s), polypeptide(s), peptide(s), enzyme(s), a ribozyme, a peptide nucleic acid, a siRNA, an RNAi, an antisense oligonucleotide, an antisense polynucleotide, antibodies, antigen binding fragments, as well as variants, and/or active fragments thereof, for use in the treatment, prophylaxis, and/or amelioration of one or more symptoms of a mammalian disease, dysfunction, injury, and/or disorder). polypeptide, a peptide, an antibody, an antigen binding fragment.

In some embodiments, the disclosure provides rAAV particles as described herein comprising rAAV nucleic acid vectors that comprise at least a first nucleic acid segment that encodes one or more therapeutic agents that alter, inhibit, reduce, prevent, eliminate, or impair the activity of one or more endogenous biological processes in the cell. In particular embodiments, such therapeutic agents may be those that selectively inhibit or reduce the effects of one or more metabolic processes, dysfunctions, disorders, or diseases. In certain embodiments, the defect may be caused by injury or trauma to the mammal for which treatment is desired. In other embodiments, the defect may be caused by the overexpression of an endogenous biological compound, while in other embodiments still, the defect may be caused by the under-expression or even lack of one or more endogenous biological compounds.

When the use of such nucleic acid vectors is contemplated for introduction of one or more exogenous proteins, polypeptides, peptides, ribozymes, siRNAs, and/or antisense oligonucleotides, to a particular cell transfected with the nucleic acid vector, one may employ the AAV nucleic acid vectors disclosed herein by incorporating into the vector at least a first exogenous polynucleotide operably positioned downstream and under the control of at least a first heterologous promoter that expresses the polynucleotide in a cell comprising the vector to produce the encoded therapeutic agent, including for example, peptides, proteins, polypeptides, antibodies, ribozymes, siRNAs, and antisense oligo- or polynucleotides. Such constructs may employ one or more heterologous promoters to express the therapeutic agent of interest. Such promoters may be constitutive, inducible, or even cell- or tissue-specific. Exemplary promoters include, but are not limited to, a CMV promoter, a β-actin promoter, a hybrid CMV promoter, a hybrid β-actin promoter, an EF1 promoter, a U1a promoter, a U1b promoter, a Tet-inducible promoter, a VP16-LexA promoter, human parvovirus B19 promoter, a joint-specific promoter and a human-specific promoter.

The rAAV nucleic acid vectors of the disclosure may also further comprise a second nucleic acid segment that comprises, consists essentially of, or consists of, one or more enhancers, regulatory elements, transcriptional elements, to alter or effect transcription of the heterologous gene cloned in the rAAV nucleic acid vectors. For example, the rAAV nucleic acid vectors of the disclosure may further comprise a second nucleic acid segment that comprises, consists essentially of, or consists of, at least a first CMV enhancer, a synthetic enhancer, or a cell- or tissue-specific enhancer. The second nucleic acid segment may also further comprise, consist essentially of, or consist of one or more intron sequences, post-transcriptional regulatory elements, or such like. The nucleic acid vectors of the disclosure may also optionally further comprise a third nucleic acid segment that comprises, consists essentially of, or consists of, one or more polylinker or multiple restriction sites/cloning region(s) to facilitate insertion of one or more selected genetic elements, polynucleotides, and the like into the rAAV nucleic acid vectors at a convenient restriction site.

In aspects of the disclosure, the exogenous polynucleotides that are comprised within one or more of the rAAV nucleic acid vectors disclosed herein are preferably of mammalian origin, with polynucleotides encoding nucleic acids, polypeptides and peptides of human, primate, murine, porcine, bovine, ovine, feline, canine, equine, epine, caprine, or lupine origin being particularly preferred.

As described herein, the exogenous polynucleotide will preferably encode one or more proteins, polypeptides, peptides, enzymes, antibodies, siRNAs, ribozymes, antisense polynucleotides or oligonucleotides, PNA molecules, or a combination of two or more of these therapeutic agents. In fact, the exogenous polynucleotide may encode two or more such molecules, or a plurality of such molecules as may be desired. When combinational gene therapies are desired, two or more different molecules may be produced from a single rAAV expression system, or alternatively, a selected host cell may be transfected with two or more unique rAAV expression systems, each of which may comprise one or more distinct polynucleotides that encode a therapeutic agent.

In other embodiments, the disclosure also provides rAAV nucleic acid vectors that are comprised within an infectious rAAV viral particle (e.g., an rAAV viral particle comprising a modified capsid protein as described herein), or pluralities of such particles, which themselves may also be comprised within one or more diluents, buffers, physiological solutions or pharmaceutical vehicles, formulated for administration to a mammal such as a human for therapeutic, and/or prophylactic gene therapy regimens. Such nucleic acid vectors or rAAV particles, and pluralities thereof may also be provided in excipient formulations that are acceptable for veterinary administration to selected livestock, exotic or domesticated animals, companion animals (including pets and such like), as well as non-human primates, zoological or otherwise captive specimens, and such like, wherein the use of such nucleic acid vectors and rAAV particles and related gene therapy is indicated to produce a beneficial effect upon administration to such an animal.

The disclosure also concerns host cells that comprise at least one of the disclosed rAAV particles or rAAV vectors. Such host cells include mammalian host cells, with human host cells being preferred, and may be either isolated, in cell or tissue culture. In the case of genetically modified animal models (e.g., a mouse or dog), the transformed host cells may be comprised within the body of a non-human animal itself.

Also provided herein is a method for the production of the rAAV particles described herein. In some embodiments, it is contemplated that one very significant advantage of the disclosed viral particles will be the ability to utilize lower titers of viral particles in mammalian transduction protocols, yet still retain transfection rates at a suitable level.

Compositions comprising one or more of the disclosed rAAV particles, rAAV nucleic acid vectors or host cells are also provided, and particularly those compositions that further comprise at least a first pharmaceutically-acceptable excipient for use in therapy, and for use in the manufacture of medicaments for the treatment of one or more mammalian diseases, disorders, dysfunctions, or trauma. Such pharmaceutical compositions may optionally further comprise one or more diluents, buffers, liposomes, a lipid, a lipid complex, or the rAAV particles may be comprised within a microsphere or a nanoparticle. Pharmaceutical formulations suitable for intramuscular, intravenous, or direct injection into an organ or tissue or a plurality of cells or tissues of a human or other mammal are particularly preferred, however, the compositions disclosed herein may also find utility in administration to discreet areas of the mammalian body, including for example, formulations that are suitable for direct injection into one or more organs, tissues, or cell types in the body. Such injection sites include, but are not limited to, a tissue such as a muscle or epithelium, or an organ such as the eye, or other site within a subject's body.

Also provided by the disclosure are kits comprising one or more of the disclosed rAAV particles, vectors, proteins, transformed host cells or pharmaceutical compositions comprising such; and instructions for using the kit in a therapeutic, diagnostic, or clinical embodiment. Such kits may further comprise one or more reagents, restriction enzymes, peptides, therapeutics, pharmaceutical compounds, or means for delivery of the composition(s) to host cells, or to an animal (e.g., syringes, injectables, and the like). Such kits may be therapeutic kits for treating, preventing, or ameliorating the symptoms of a disease, deficiency, dysfunction, and/or injury, and may comprise one or more of the nucleic acid vectors, proteins, rAAV particles, or a plurality of such particles, and instructions for using the kit in a therapeutic and/or diagnostic medical regimen. Such kits may also be used in large-scale production methodologies to produce large quantities of the viral particles themselves for commercial sale, or for use by others, including e.g., virologists, medical professionals, and the like.

Another important aspect of the present disclosure concerns methods of use of the disclosed rAAV particles, nucleic acid vectors, protein compositions, and host cells described herein in the preparation of medicaments for preventing, treating or ameliorating the symptoms of various diseases, dysfunctions, or deficiencies in an animal, such as a vertebrate mammal. Such methods generally involve administration to a mammal, such as a human in need thereof, one or more of the disclosed viral particles, nucleic acid vectors, host cells, compositions, or pluralities thereof, in an amount and for a time sufficient to prevent, treat, or lessen the symptoms of such a disease, dysfunction, or deficiency in the affected animal. The methods may also encompass prophylactic treatment of animals suspected of having such conditions, or administration of such compositions to those animals at risk for developing such conditions either following diagnosis, or prior to the onset of symptoms.

In other embodiments, the disclosure also provides the disclosed rAAV nucleic acid vectors comprised within a rAAV particle, comprised within one or more pharmaceutical carriers, and may be formulated for administration to a mammal such as a human for therapeutic, and/or prophylactic gene therapy regimens. Such vectors may also be provided in pharmaceutical formulations that are acceptable for veterinary administration to selected livestock, domesticated animals, pets, and the like.

Another aspect of the present disclosure concerns methods of use of the disclosed vectors, viral particles, compositions, and host cells described herein in the preparation of medicaments for treating or ameliorating the symptoms of various polypeptide deficiencies in a mammal. Such methods generally involve administration to a mammal, or human in need thereof, one or more of the disclosed nucleic acid vectors, viral particles, host cells, or compositions, in an amount and for a time sufficient to treat or ameliorate the symptoms of such a deficiency in the affected mammal. The methods may also encompass prophylactic treatment of animals suspected of having such conditions, or administration of such compositions to those animals at risk for developing such conditions either following diagnosis, or prior to the onset of symptoms.

The details of one or more embodiments of the disclosure are set forth in the description below. Other features or advantages of the present disclosure will be apparent from the following drawings and detailed description of several embodiments, and also from the appending claims.

BRIEF DESCRIPTION OF THE SEQUENCES

SEQ ID NO:1 is an exemplary amino acid sequence of the capsid protein of the wild-type adeno-associated virus serotype 1 (AAV1);

SEQ ID NO:2 is an exemplary amino acid sequence of the capsid protein of the wild-type adeno-associated virus serotype 5 (AAV5);

SEQ ID NO:3 is an exemplary amino acid sequence of the capsid protein of the wild-type adeno-associated virus serotype 6 (AAV6).

(exemplary positions Y705, Y731, and T492 are each bolded, underlined, and italicized)

SEQ ID NO: 1

```
  1 MAADGYLPDW LEDNLSEGIR EWWDLKPGAP KPKANQQKQD DGRGLVLPGY
 51 KYLGPFNGLD KGEPVNAADA AALEHDKAYD QQLKAGDNPY LRYNHADAEF
101 QERLQEDTSF GGNLGRAVFQ AKKRVLEPLG LVEEGAKTAP GKKRPVEQSP
151 QEPDSSSGIG KTGQQPAKKR LNFGQTGDSE SVPDPQPLGE PPATPAAVGP
201 TTMASGGGAP MADNNEGADG VGNASGNWHC DSTWLGDRVI TTSTRTWALP
251 TYNNHLYKQI SSASTGASND NHYFGYSTPW GYFDFNRFHC HFSPRDWQRL
301 INNNWGFRPK RLNFKLFNIQ VKEVTTNDGV TTIANNLTST VQVFSDSEYQ
351 LPYVLGSAHQ GCLPPFPADV FMIPQYGYLT LNNGSQAVGR SSFYCLEYFP
401 SQMLRTGNNF TFSYTFEEVP FHSSYAHSQS LDRLMNPLID QYLYYLNRTQ
451 NQSGSAQNKD LLFSRGSPAG MSVQPKNWLP GPCYRQQRVS KTKTDNNNSN
501 FTWTGASKYN LNGRESIINP GTAMASHKDD EDKFFPMSGV MIFGKESAGA
551 SNTALDNVMI TDEEEIKATN PVATERFGTV AVNFQSSSTD PATGDVHAMG
601 ALPGMVWQDR DVYLQGPIWA KIPHTDGHFH PSPLMGGFGL KNPPPQILIK
651 NTPVPANPPA EFSATKFASF ITQYSTGQVS VEIEWELQKE NSKRWNPEVQ
701 YTSNYAKSAN VDFTVDNNGL YTEPRPIGTR YLTRPL
```

(exemplary positions Y436, Y693, and Y719 are each bolded, underlined, and italicized)

SEQ ID NO: 2

```
  1 MSFVDHPPDW LEEVGEGLRE FLGLEAGPPK PKPNQQHQDQ ARGLVLPGYN
 51 YLGPGNGLDR GEPVNRADEV AREHDISYNE QLEAGDNPYL KYNHADAEFQ
101 EKLADDTSFG GNLGKAVFQA KKRVLEPFGL VEEGAKTAPT GKRIDDHFPK
151 RKKARTEEDS KPSTSSDAEA GPSGSQQLQI PAQPASSLGA DTMSAGGGGP
201 LGDNNQGADG VGNASGDWHC DSTWMGDRVV TKSTRTWVLP SYNNHQYREI
251 KSGSVDGSNA NAYFGYSTPW GYFDFNRFHS HWSPRDWQRL INNYWGFRPR
301 SLRVKIFNIQ VKEVTVQDST TTIANNLTST VQVFTDDDYQ LPYVVGNGTE
351 GCLPAFPPQV FTLPQYGYAT LNRDNTENPT ERSSFFCLEY FPSKMLRTGN
```

```
                              -continued
401 NFEFTYNFEE  VPFHSSFAPS  QNLFKLANPL  VDQYL*Y*RFVS  TNNTGGVQFN

451 KNLAGRYANT  YKNWFPGPMG  RTQGWNLGSG  VNRASVSAFA   TTNRMELEGA

501 SYQVPPQPNG  MTNNLQGSNT  YALENTMIFN  SQPANPGTTA   TYLEGNMLIT

551 SESETQPVNR  VAYNVGGQMA  TNNQSSTTAP  ATGTYNLQEI   VPGSVWMERD

601 VYLQGPIWAK  IPETGAHFHP  SPAMGGFGLK  HPPPMMLIKN   TPVPGNITSF

651 SDVPVSSFIT  QYSTGQVTVE  MEWELKKENS  KRWNPEIQYT   NN*Y*NDPQFVD

701 FAPDSTGEYR  TTRPIGTR*Y*L  TRPL (exemplary positions Y705, Y731, and T492 are each bolded, underlined,
and italicized)
                                                    SEQ ID NO: 3
  1 MAADGYLPDW  LEDNLSEGIR  EWWDLKPGAP  KPKANQQKQD   DGRGLVLPGY

51 KYLGPFNGLD  KGEPVNAADA  AALEHDKAYD  QQLKAGDNPY   LRYNHADAEF

101 QERLQEDTSF  GGNLGRAVFQ  AKKRVLEPFG  LVEEGAKTAP   GKKRPVEQSP

151 QEPDSSSGIG  KTGQQPAKKR  LNFGQTGDSE  SVPDPQPLGE   PPATPAAVGP

201 TTMASGGGAP  MADNNEGADG  VGNASGNWHC  DSTWLGDRVI   TTSTRTWALP

251 TYNNHLYKQI  SSASTGASND  NHYFGYSTPW  GYFDFNRFHC   HFSPRDWQRL

301 INNNWGFRPK  RLNFKLFNIQ  VKEVTTNDGV  TTIANNLTST   VQVFSDSEYQ

351 LPYVLGSAHQ  GCLPPFPADV  FMIPQYGYLT  LNNGSQAVGR   SSFYCLEYFP

401 SQMLRTGNNF  TFSYTFEDVP  FHSSYAHSQS  LDRLMNPLID   QYLYFLNRTQ

451 NQSGSAQNKD  LLFSRGSPAG  MSVQPKNWLP  GPCYRQQRVS   K*T*KTDNNNSN

501 FTWTGASKYN  LNGRESIINP  GTAMASHKDD  KDKFFPMSGV   MIFGKESAGA

551 SNTALDNVMI  TDEEEIKATN  PVATERFGTV  AVNLQSSSTD   PATGDVHVMG

601 ALPGMVWQDR  DVYLQGPIWA  KIPHTDGHFH  PSPLMGGFGL   KHPPPQILIK

651 NTPVPANPPA  EFSATKFASF  ITQYSTGQVS  VEIEWELQKE   NSKRWNPEVQ

701 YTSNYAKSAN  VDFTVDNNGL  YTEPRPIGTR  *Y*LTRPL
```

BRIEF DESCRIPTION OF THE DRAWINGS

The following drawings form part of the present specification and are included to further demonstrate certain aspects of the present disclosure, which can be better understood by reference to one or more of these drawings in combination with the detailed description of specific embodiments presented herein.

DETAILED DESCRIPTION OF THE INVENTION

Figure 1A:
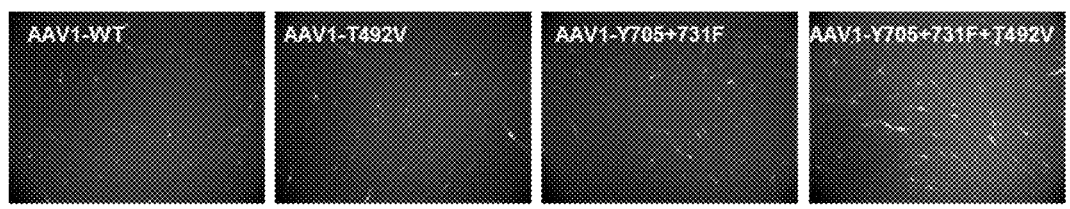
FIG. 1A is a series of photographs and a graph showing EGFP expression in a murine muscle cell line treated with wild-type (WT) or mutant AAV1 vectors.
Figure 1A:
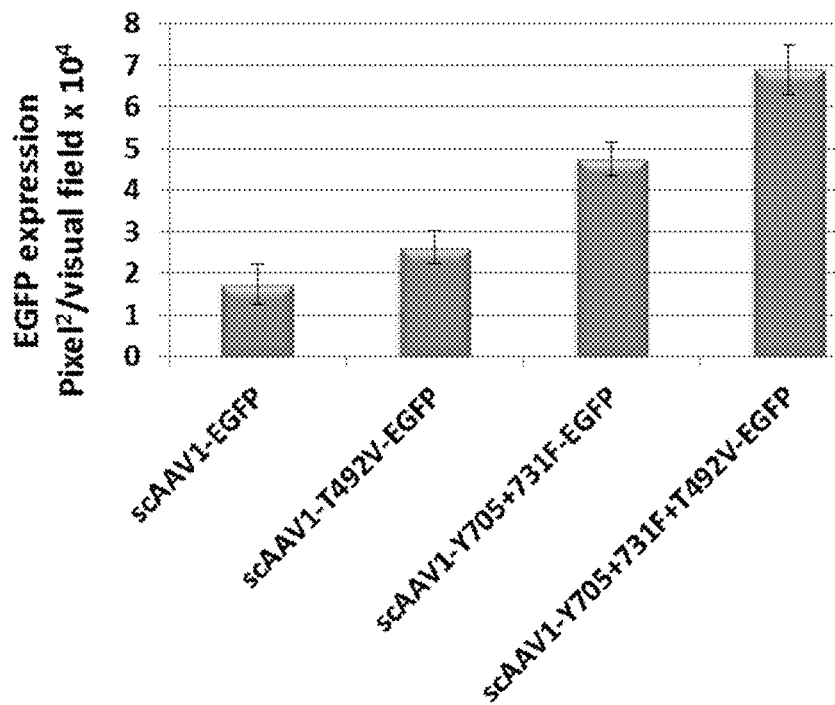

The present disclosure provides AAV capsid proteins comprising modifications of one or more of a combination of the surface-exposed threonine and/or tyrosine residues in the VP3 region. Also provided are rAAV particles that include one or more of the AAV capsid protein mutations disclosed herein, as well as nucleic acid molecules encoding the AAV capsid proteins disclosed herein. Advantageously, the rAAV particles of the present disclosure have improved transduction efficiency in a variety of cells, tissues and organs of interest, when compared to rAAV viral particles comprising wild-type capsid proteins. In particular, as described herein, it was found that rAAV particles comprising a modified AAV1 capsid protein having three mutations at Y705F+Y731F+T492V efficiently transduced muscle. It was also found that rAAV particles comprising a modified AAV5 capsid protein having three mutations at Y436F+Y693F+Y719F efficiently transduced retinal cells and airway epithelial cells. Lastly, it was found that rAAV particles comprising a modified AAV6 capsid protein having three mutations at Y705F+Y731F+T492V efficiently transduced multiple cells and tissues including hematopoietic stem cells, dendritic cells, monocytes, airway epithelial cells, muscle, liver, pancreas and microglial cells. Accordingly, aspects of the disclosure relate to rAAV particles, capsid proteins, nucleic acid vectors, host cells, compositions, kits, and uses thereof.

Recombinant AAV Vectors and Viral Particles

One aspect of the disclosure provides AAV capsid proteins, such as AAV VP3 capsid proteins, or VP1 or VP2 capsid proteins comprising a VP3 region, comprising modifications of a combination of the surface-exposed threonine and/or tyrosine residues. Also provided are rAAV particles comprising the AAV capsid proteins, as well as nucleic acid molecules encoding the AAV capsid proteins of the present disclosure. Advantageously, the rAAV particles described herein have improved efficiency in transduction of a variety of cells, tissues and organs of interest, when compared to rAAV particles comprising wild-type AAV capsid proteins.

In some embodiments, the present disclosure provides a nucleic acid molecule comprising a nucleotide sequence encoding an AAV capsid protein (e.g., an AAV1, AAV5, or AAV6 capsid protein), wherein the AAV capsid protein comprises modifications of a combination of the surface-exposed threonine and/or tyrosine residues at positions within the VP3 region.

In one embodiment, the nucleic acid molecule comprises a nucleotide sequence encoding an AAV capsid protein, the AAV capsid protein comprising one of the following modifications in the VP3 region:

(i) a non-tyrosine residue at one or more of or at each of the positions that correspond to Y705 and Y731 of a wild-type AAV1 capsid protein (e.g., SEQ ID NO: 1) and a non-threonine residue at a position that corresponds to T492 in the wild-type AAV1 protein;

(ii) a chemically-modified tyrosine residue at one or more of or at each of the positions that correspond to Y705 and Y731 of a wild-type AAV1 capsid protein (e.g., SEQ ID NO: 1) and a chemically-modified threonine residue at a position that corresponds to T492 of the wild-type AAV1 capsid protein;

(iii) a non-tyrosine residue at one or more of or at each of the positions that correspond to Y436F, Y693F, and Y719F of a wild-type AAV5 capsid protein (e.g., SEQ ID NO: 2);

(iv) a chemically-modified tyrosine residue at one or more of or at each of the positions that correspond to Y436F, Y693F, and Y719F of a wild-type AAV5 capsid protein (e.g., SEQ ID NO: 2);

(v) a non-tyrosine residue at one or more of or at each of the positions that correspond to Y705 and Y731 of a wild-type AAV6 capsid protein (e.g., SEQ ID NO: 3) and a non-threonine residue at a position that corresponds to T492 of the wild-type AAV6 capsid protein; or (vi) a chemically-modified tyrosine residue at one or more of or at each of the positions that correspond to Y705 and Y731 of a wild-type AAV6 capsid protein (e.g., SEQ ID NO: 3) and a chemically-modified threonine residue at a position that corresponds to T492 of the wild-type AAV6 capsid protein.

In some embodiments, the present disclosure provides an AAV capsid protein (e.g., an AAV1, AAV5, or AAV6 capsid protein), wherein the AAV capsid protein comprises modifications of a combination of the surface-exposed threonine and/or tyrosine residues at positions within the VP3 region.

In one embodiment, the AAV capsid protein comprises one of the following modifications in the VP3 region:

(i) a non-tyrosine residue at one or more of or at each of the positions that correspond to Y705 and Y731 of a wild-type AAV1 capsid protein (e.g., SEQ ID NO: 1) and a non-threonine residue at a position that corresponds to T492 in the wild-type AAV1 protein;

(ii) a chemically-modified tyrosine residue at one or more of or at each of the positions that correspond to Y705 and Y731 of a wild-type AAV1 capsid protein (e.g., SEQ ID NO: 1) and a chemically-modified threonine residue at a position that corresponds to T492 of the wild-type AAV1 capsid protein;

(iii) a non-tyrosine residue at one or more of or at each of the positions that correspond to Y436F, Y693F, and Y719F of a wild-type AAV5 capsid protein (e.g., SEQ ID NO: 2);

(iv) a chemically-modified tyrosine residue at one or more of or at each of the positions that correspond to Y436F, Y693F, and Y719F of a wild-type AAV5 capsid protein (e.g., SEQ ID NO: 2);

(v) a non-tyrosine residue at one or more of or at each of the positions that correspond to Y705 and Y731 of a wild-type AAV6 capsid protein (e.g., SEQ ID NO: 3) and a non-threonine residue at a position that corresponds to T492 of the wild-type AAV6 capsid protein; or (vi) a chemically-modified tyrosine residue at one or more of or at each of the positions that correspond to Y705 and Y731 of a wild-type AAV6 capsid protein (e.g., SEQ ID NO: 3) and a chemically-modified threonine residue at a position that corresponds to T492 of the wild-type AAV6 capsid protein.

In some embodiments, the present disclosure provides an rAAV particle comprising an AAV capsid protein (e.g., an AAV1, AAV5, or AAV6 capsid protein), wherein the AAV capsid protein comprises modifications of a combination of the surface-exposed threonine and/or tyrosine residues at positions within the VP3 region.

In one embodiment, the rAAV particle comprises an AAV capsid protein, the AAV capsid protein comprising one of the following modifications in the VP3 region:

(i) a non-tyrosine residue at one or more of or at each of the positions that correspond to Y705 and Y731 of a wild-type AAV1 capsid protein (e.g., SEQ ID NO: 1) and a non-threonine residue at a position that corresponds to T492 in the wild-type AAV1 protein;

(ii) a chemically-modified tyrosine residue at one or more of or at each of the positions that correspond to Y705 and Y731 of a wild-type AAV1 capsid protein (e.g., SEQ ID NO: 1) and a chemically-modified threonine residue at a position that corresponds to T492 of the wild-type AAV1 capsid protein;

(iii) a non-tyrosine residue at one or more of or at each of the positions that correspond to Y436F, Y693F, and Y719F of a wild-type AAV5 capsid protein (e.g., SEQ ID NO: 2);

(iv) a chemically-modified tyrosine residue at one or more of or at each of the positions that correspond to Y436F, Y693F, and Y719F of a wild-type AAV5 capsid protein (e.g., SEQ ID NO: 2);

(v) a non-tyrosine residue at one or more of or at each of the positions that correspond to Y705 and Y731 of a wild-type AAV6 capsid protein (e.g., SEQ ID NO: 3) and a non-threonine residue at a position that corresponds to T492 of the wild-type AAV6 capsid protein; or (vi) a chemically-modified tyrosine residue at one or more of or at each of the positions that correspond to Y705 and Y731 of a wild-type AAV6 capsid protein (e.g., SEQ ID NO: 3) and a chemically-modified threonine residue at a position that corresponds to T492 of the wild-type AAV6 capsid protein.

In some embodiments, modified AAV capsid protein does not result in phosphorylation and/or ubiquitination of an rAAV particle comprising the capsid protein and/or increases the efficiency of transduction of such a viral particle into a cell or tissue compared to a rAAV particle comprising a corresponding wild-type capsid protein (e.g., a AAV1, AAV5, or AAV6 wild-type capsid protein, such as SEQ ID NOs:1-3).

In one embodiment, the nucleic acid molecule comprises a nucleotide sequence encoding an AAV capsid protein (e.g., a VP3 capsid protein), wherein the AAV serotype is selected from AAV1, AAV5, and AAV6. In certain embodiments, the wild-type AAV capsid protein has an amino acid sequence selected from SEQ ID NOs: 1-3.

In some embodiments, the nucleic acid molecule comprises a nucleotide sequence encoding an AAV1 capsid protein. The adeno-associated virus 1 (AAV1) is a non-pathogenic human parvovirus. Recombinant AAV1 vectors are currently in use in Phase I/II clinical trials for gene therapy of a number of diseases such as alpha-1 antitrypsin deficiency, LPL deficiency, Pompe's disease and muscular dystrophy. In some embodiments, the nucleic acid molecule comprises a nucleotide sequence encoding an AAV5 capsid protein. Recombinant AAV5 vectors are currently in use in Phase I/II clinical trials for gene therapy of diseases such as Acute Intermittent Porphyria. In some embodiments, the nucleic acid molecule comprises a nucleotide sequence encoding an AAV6 capsid protein. Recombinant AAV6 vectors are currently in use in Phase I/II clinical trials for gene therapy of diseases such as severe heart failure.

In one embodiment, a surface-exposed threonine residue corresponding to a threonine residue of a wild-type AAV capsid sequence described herein (e.g., SEQ ID NOs:1-3) is modified into a non-threonine residue and/or is chemically modified so that said non-threonine residue or said modified threonine residue does not result in phosphorylation and/or ubiquitination of an AAV viral particle. In some embodiments, the surface-exposed threonine residue of the AAV capsid is modified into valine (V).

In some embodiments, a surface-exposed tyrosine residue corresponding to a tyrosine residue of a wild-type AAV capsid sequence described herein (e.g., SEQ ID NOs:1-3) is modified into a non-tyrosine residue and/or is chemically modified so that said non-tyrosine residue or said modified tyrosine residue does not result in phosphorylation and/or ubiquitination of an AAV viral particle. In some embodiments, the surface-exposed tyrosine residue of the AAV capsid is modified into phenylalanine (F).

In some embodiments, the disclosure provides a rAAV particle comprising an AAV capsid protein described herein (e.g., a Y705F+Y731F+T492V AAV1 modified capsid protein, a Y436F+Y693F+Y719F AAV5 modified capsid protein, or a Y705F+Y731F+T492V AAV6 modified capsid protein). In some embodiments, a rAAV particle comprises a AAV nucleic acid vector described herein and a capsid comprising the modified capsid protein (e.g., a Y705F+Y731F+T492V AAV1 modified capsid protein, a Y436F+Y693F+Y719F AAV5 modified capsid protein, or a Y705F+Y731F+T492V AAV6 modified capsid protein), wherein the capsid encapsidates the AAV nucleic acid vector. In one embodiment, the rAAV particle has enhanced transduction efficiency, when compared to the wild-type rAAV particle. In another embodiment, the rAAV particle is capable of efficient transduction of cells, tissues, and/or organs of interest.

In some embodiments, the rAAV nucleic acid vector comprises inverted terminal repeat sequences (ITRs), such as those derived from a wild-type AAV genome, such as the AAV2 genome. In some embodiments, the rAAV nucleic acid vector further comprises a transgene (also referred to as a heterologous nucleic acid molecule) operably linked to a promoter and optionally, other regulatory elements, wherein the ITRs flank the transgene. In some embodiments, the rAAV nucleic acid vector comprises a transgene, wherein the transgene is a gene of interest operatively linked to a promoter (e.g., a heterologous promoter, for example, a promoter sequence non-native to the gene of interest) and flanked by ITRs. In one embodiment, the transgene encodes a therapeutic agent of interest.

Exemplary promoters include one or more heterologous, tissue-specific, constitutive or inducible promoters, including, but not limited to, a promoter selected from the group consisting of cytomegalovirus (CMV) promoters, desmin (DES), beta-actin promoters, insulin promoters, enolase promoters, BDNF promoters, NGF promoters, EGF promoters, growth factor promoters, axon-specific promoters, dendrite-specific promoters, brain-specific promoters, hippocampal-specific promoters, kidney-specific promoters, elafin promoters, cytokine promoters, interferon promoters, growth factor promoters, alpha-1 antitrypsin promoters, brain-specific promoters, neural cell-specific promoters, central nervous system cell-specific promoters, peripheral nervous system cell-specific promoters, interleukin promoters, serpin promoters, hybrid CMV promoters, hybrid beta-actin promoters, EF1 promoters, U1a promoters, U1b promoters, Tet-inducible promoters and VP16-LexA promoters. In exemplary embodiments, the promoter is a mammalian or avian beta-actin promoter.

Exemplary enhancer sequences include, but are not limited to, one or more selected from the group consisting of CMV enhancers, synthetic enhancers, liver-specific enhancers, vascular-specific enhancers, brain-specific enhancers, neural cell-specific enhancers, lung-specific enhancers, muscle-specific enhancers, kidney-specific enhancers, pancreas-specific enhancers, and islet cell-specific enhancers.

Exemplary therapeutic agents include, but are not limited to, an agent selected from the group consisting of polypeptides, peptides, antibodies, antigen binding fragments, ribozymes, peptide nucleic acids, siRNA, RNAi, antisense oligonucleotides and antisense polynucleotides.

In exemplary embodiments, the rAAV nucleic acid vectors of the disclosure encode a therapeutic protein or polypeptide (e.g., as a transgene operatively linked to a heterologous promoter, for example, a promoter sequence non-native to the transgene) selected from the group consisting of adrenergic agonists, anti-apoptosis factors, apoptosis inhibitors, cytokine receptors, cytokines, cytotoxins, erythropoietic agents, glutamic acid decarboxylases, glycoproteins, growth factors, growth factor receptors, hormones, hormone receptors, interferons, interleukins, interleukin receptors, kinases, kinase inhibitors, nerve growth factors, netrins, neuroactive peptides, neuroactive peptide receptors, neurogenic factors, neurogenic factor receptors, neuropilins, neurotrophic factors, neurotrophins, neurotrophin receptors, N-methyl-D-aspartate antagonists, plexins, proteases, protease inhibitors, protein decarboxylases, protein kinases, protein kinsase inhibitors, proteolytic proteins, proteolytic protein inhibitors, semaphorin a semaphorin receptors, serotonin transport proteins, serotonin uptake inhibitors, serotonin receptors, serpins, serpin receptors, and tumor suppressors.

In exemplary embodiments, the rAAV nucleic acid vectors may comprise a nucleic acid segment that encodes a polypeptide selected from the group consisting of BDNF, CNTF, CSF, EGF, FGF, G-SCF, GM-CSF, gonadotropin, IFN, IFG-1, M-CSF, NGF, PDGF, PEDF, TGF, TGF-B2, TNF, VEGF, prolactin, somatotropin, XIAP1, IL-1, IL-2, IL-3, IL-4, IL-5, IL-6, IL-7, IL-8, IL-9, IL-10, IL-10(187A), viral IL-10, IL-11, IL-12, IL-13, IL-14, IL-15, IL-16, IL-17, and IL-18. Such therapeutic agents may be of human, murine, avian, porcine, bovine, ovine, feline, canine, equine, epine, caprine, lupine or primate origin.

Exemplary rAAV nucleic acid vectors useful according to the disclosure include single-stranded (ss) or self-complementary (sc) AAV nucleic acid vectors.

The rAAV nucleic acid vectors or rAAV particles of the present disclosure may also be within an isolated mammalian host cell, including for example, human, primate, murine, feline, canine, porcine, ovine, bovine, equine, epine, caprine and lupine host cells. The rAAV nucleic acid vectors or rAAV particles may be within an isolated mammalian host cell such as a human endothelial, epithelial, vascular, liver, lung, heart, pancreas, intestinal, kidney, cardiac, cancer or tumor, muscle, bone, neural, blood, or brain cell.

The rAAV particle may be of any AAV serotype, including any derivative or pseudotype (e.g., 1, 2, 3, 4, 5, 6, 7, 8, 9, 10, 11, 12, or 13, or pseudotypes/derivatives thereof). For example, any ITR sequence derived or modified from an AAV serotype (e.g., 1, 2, 3, 4, 5, 6, 7, 8, 9, 10, 11, 12, or 13) can be used with viral particles comprising capsid proteins of a different serotype (e.g., 1, 2, 3, 4, 5, 6, 7, 8, 9, 10, 11, 12, or 13, or derivatives thereof).

Methods of producing rAAV particles and nucleic acid vectors are also known in the art and commercially available (see, e.g., Zolotukhin et al. Production and purification of serotype 1, 2, and 5 recombinant adeno-associated viral vectors. Methods 28 (2002) 158-167; and U.S. Patent Publication Numbers US20070015238 and US20120322861, which are incorporated herein by reference; and plasmids and kits available from ATCC and Cell Biolabs, Inc.). For example, a plasmid containing the nucleic acid vector may be combined with one or more helper plasmids, e.g., that contain a rep gene (e.g., encoding Rep78, Rep68, Rep52 and Rep40) and a cap gene (encoding VP1, VP2, and VP3, including a modified VP3 region as described herein), and transfected into a producer cell line such that the rAAV particle can be packaged and subsequently purified.

In some embodiments, the one or more helper plasmids is a first helper plasmid comprising a rep gene and a cap gene and a second helper plasmid comprising a E1a gene, a E1b gene, a E4 gene, a E2a gene, and a VA gene. In some embodiments, the rep gene is a rep gene derived from AAV2 and the cap gene is derived from AAV1, AAV5, and AAV6 and includes modifications to the gene in order to produce the modified capsid protein described herein. Helper plasmids, and methods of making such plasmids, are known in the art and commercially available (see, e.g., pDM, pDG, pDP1rs, pDP2rs, pDP3rs, pDP4rs, pDP5rs, pDP6rs, pDG (R484E/R585E), and pDP8.ape plasmids from PlasmidFactory, Bielefeld, Germany; other products and services available from Vector Biolabs, Philadelphia, Pa.; Cellbiolabs, San Diego, Calif.; Agilent Technologies, Santa Clara, Calif.; and Addgene, Cambridge, Mass.; pxx6; Grimm et al. (1998), Novel Tools for Production and Purification of Recombinant Adenoassociated Virus Vectors, Human Gene Therapy, Vol. 9, 2745-2760; Kern, A. et al. (2003), Identification of a Heparin-Binding Motif on Adeno-Associated Virus Type 2 Capsids, Journal of Virology, Vol. 77, 11072-11081.; Grimm et al. (2003), Helper Virus-Free, Optically Controllable, and Two-Plasmid-Based Production of Adeno-associated Virus Vectors of Serotypes 1 to 6, Molecular Therapy, Vol. 7, 839-850; Kronenberg et al. (2005), A Conformational Change in the Adeno-Associated Virus Type 2 Capsid Leads to the Exposure of Hidden VP1 N Termini, Journal of Virology, Vol. 79, 5296-5303; and Moullier, P. and Snyder, R. O. (2008), International efforts for recombinant adeno-associated viral vector reference standards, Molecular Therapy, Vol. 16, 1185-1188).

An exemplary, non-limiting, rAAV particle production method is described next. One or more helper plasmids are produced or obtained, which comprise rep and cap ORFs for the desired AAV serotype and the adenoviral VA, E2A (DBP), and E4 genes under the transcriptional control of their native promoters. The cap ORF may also comprise one or more modifications to produce a modified capsid protein as described herein. HEK293 cells (available from ATCC®) are transfected via CaPO4-mediated transfection, lipids or polymeric molecules such as Polyethylenimine (PEI) with the helper plasmid(s) and a plasmid containing a nucleic acid vector described herein. The HEK293 cells are then incubated for at least 60 hours to allow for rAAV particle production. Alternatively, in another example Sf9-based producer stable cell lines are infected with a single recombinant baculovirus containing the nucleic acid vector. As a further alternative, in another example HEK293 or BHK cell lines are infected with a HSV containing the nucleic acid vector and optionally one or more helper HSVs containing rep and cap ORFs as described herein and the adenoviral VA, E2A (DBP), and E4 genes under the transcriptional control of their native promoters. The HEK293, BHK, or Sf9 cells are then incubated for at least 60 hours to allow for rAAV particle production. The rAAV particles can then be purified using any method known the art or described herein, e.g., by iodixanol step gradient, CsCl gradient, chromatography, or polyethylene glycol (PEG) precipitation.

Exemplary nucleic acid sequences for producing mutated AAV1, AAV5 and AAV6 capsid proteins as described herein are provided below.

```
AAV1 (SEQ ID NO: 4):
ATGGCTGCCGATGGTTATCTTCCAGATTGGCTCGAGGACAACCTCTCTGA

GGGCATTCGCGAGTGGTGGGACTTGAAACCTGGAGCCCCGAAGCCCAAAG

CCAACCAGCAAAAGCAGGACGACGGCCGGGGTCTGGTGCTTCCTGGCTAC

AAGTACCTCGGACCCTTCAACGGACTCGACAAGGGGGAGCCCGTCAACGC

GGCGGACGCAGCGGCCCTCGAGCACGACAAGGCCTACGACCAGCAGCTCA

AAGCGGGTGACAATCCGTACCTGCGGTATAACCACGCCGACGCCGAGTTT

CAGGAGCGTCTGCAAGAAGATACGTCTTTTGGGGGCAACCTCGGGCGAGC

AGTCTTCCAGGCCAAGAAGCGGGTTCTCGAACCTCTCGGTCTGGTTGAGG

AAGGCGCTAAGACGGCTCCTGGAAAGAAACGTCCGGTAGAGCAGTCGCCA

CAAGAGCCAGACTCCTCCTCGGGCATCGGCAAGACAGGCCAGCAGCCCGC
```

```
TAAAAAGAGACTCAATTTTGGTCAGACTGGCGACTCAGAGTCAGTCCCCG
ATCCACAACCTCTCGGAGAACCTCCAGCAACCCCGCTGCTGTGGGACCT
ACTACAATGGCTTCAGGCGGTGGCGCACCAATGGCAGACAATAACGAAGG
CGCCGACGGAGTGGGTAATGCCTCAGGAAATTGGCATTGCGATTCCACAT
GGCTGGGCGACAGAGTCATCACCACCAGCACCCGCACCTGGGCCTTGCCC
ACCTACAATAACCACCTCTACAAGCAAATCTCCAGTGCTTCAACGGGGGC
CAGCAACGACAACCACTACTTCGGCTACAGCACCCCCTGGGGGTATTTTG
ATTTCAACAGATTCCACTGCCACTTTTCACCACGTGACTGGCAGCGACTC
ATCAACAACAATTGGGGATTCCGGCCCAAGAGACTCAACTTCAAACTCTT
CAACATCCAAGTCAAGGAGGTCACGACGAATGATGGCGTCACAACCATCG
CTAATAACCTTACCAGCACGGTTCAAGTCTTCTCGGACTCGGAGTACCAG
CTTCCGTACGTCCTCGGCTCTGCGCACCAGGGCTGCCTCCCTCCGTTCCC
GGCGGACGTGTTCATGATTCCGCAATACGGCTACCTGACGCTCAACAATG
GCAGCCAAGCCGTGGGACGTTCATCCTTTTACTGCCTGGAATATTTCCCT
TCTCAGATGCTGAGAACGGGCAACAACTTTACCTTCAGCTACACCTTTGA
GGAAGTGCCTTTCCACAGCAGCTACGCGCACAGCCAGAGCCTGGACCGGC
TGATGAATCCTCTCATCGACCAATACCTGTATTACCTGAACAGAACTCAA
AATCAGTCCGGAAGTGCCCAAAACAAGGACTTGCTGTTTAGCCGTGGGTC
TCCAGCTGGCATGTCTGTTCAGCCCAAAAACTGGCTACCTGGACCCTGTT
ATCGGCAGCAGCGCGTTTCTAAAGTAAAAACAGACAACAACAACAGCAAT
TTTACCTGGACTGGTGCTTCAAAATATAACCTCAATGGGCGTGAATCCAT
CATCAACCCTGGCACTGCTATGGCCTCACACAAAGACGACGAAGACAAGT
TCTTTCCCATGAGCGGTGTCATGATTTTTGGAAAAGAGAGCGCCGGAGCT
TCAAACACTGCATTGGACAATGTCATGATTACAGACGAAGAGGAAATTAA
AGCCACTAACCCTGTGGCCACCGAAAGATTTGGGACCGTGGCAGTCAATT
TCCAGAGCAGCAGCACAGACCCTGCGACCGGAGATGTGCATGCTATGGGA
GCATTACCTGGCATGGTGTGGCAAGATAGAGACGTGTACCTGCAGGGTCC
CATTTGGGCCAAAATTCCTCACACAGATGGACACTTTCACCCGTCTCCTC
TTATGGGCGGCTTTGGACTCAAGAACCCGCCTCCTCAGATCCTCATCAAA
AACACGCCTGTTCCTGCGAATCCTCCGGCGGAGTTTTCAGCTACAAAGTT
TGCTTCATTCATCACCCAATACTCCACAGGACAAGTGAGTGTGGAAATTG
AATGGGAGCTGCAGAAAGAAAACAGCAAGCGCTGGAATCCCGAAGTGCAG
TACACATCCAATTTTGCAAAATCTGCCAATGTTGATTTTACTGTGGACAA
CAATGGACTTTATACTGAGCCTCGCCCCATTGGCACGCGTTTCCTTACCC
GTCCCCTGTAA
AAV5 (SEQ ID NO: 5):
ATGTCTTTTGTTGATCACCCTCCAGATTGGTTGGAAGAAGTTGGTGAAGG
TCTTCGCGAGTTTTTGGGCCTTGAAGCGGGCCCACCGAAACCAAAACCCA
ATCAGCAGCATCAAGATCAAGCCCGTGGTCTTGTGCTGCCTGGTTATAAC
TATCTCGGACCCGGAAACGGTCTCGATCGAGGAGAGCCTGTCAACAGGGC
AGACGAGGTCGCGCGAGAGCACGACATCTCGTACAACGAGCAGCTTGAGG
CGGGAGACAACCCCTACCTCAAGTACAACCACGCGGACGCCGAGTTTCAG
GAGAAGCTCGCCGACGACACATCCTTCGGGGGAAACCTCGGAAAGGCAGT
CTTTCAGGCCAAGAAAAGGGTTCTCGAACCTTTTGGCCTGGTTGAAGAGG
GTGCTAAGACGGCCCCTACCGGAAAGCGGATAGACGACCACTTTCCAAAA
AGAAAGAAGGCTCGGACCGAAGAGGACTCCAAGCCTTCCACCTCGTCAGA
CGCCGAAGCTGGACCCAGCGGATCCCAGCAGCTGCAAATCCCAGCCCAAC
CAGCCTCAAGTTTGGGAGCTGATACAATGTCTGCGGGAGGTGGCGGCCCA
TTGGGCGACAATAACCAAGGTGCCGATGGAGTGGGCAATGCCTCGGGAGA
TTGGCATTGCGATTCCACGTGGATGGGGACAGAGTCGTCACCAAGTCCA
CCCGAACCTGGGTGCTGCCCAGCTACAACAACCACCAGTACCGAGAGATC
AAAAGCGGCTCCGTCGACGGAAGCAACGCCAACGCGTTCTTTGGATACAG
CACCCCCTGGGGGTACTTTGACTTTAACCGCTTCCACAGCCACTGGAGCC
CCCGAGACTGGCAAAGACTCATCAACAACTACTGGGGCTTCAGACCCCGG
TCCCTCAGAGTCAAAATCTTCAACATTCAAGTCAAAGAGGTCACGGTGCA
GGACTCCACCACCACCATCGCCAACAACCTCACCTCCACCGTCCAAGTGT
TTACGGACGACGACTACCAGCTGCCCTACGTCGTCGGCAACGGGACCGAG
GGATGCCTGCCGGCCTTCCCTCCGCAGGTCTTTACGCTGCCGCAGTACGG
TTACGCGACGCTGAACCGCGACAACACAGAAAATCCCACCGAGAGGAGCA
GCTTCTTCTGCCTAGAGTACTTTCCCAGCAAGATGCTGAGAACGGGCAAC
AACTTTGAGTTTACCTACAACTTTGAGGAGGTGCCCTTCCACTCCAGCTT
CGCTCCCAGTCAGAACCTCTTCAAGCTGGCCAACCCGCTGGTGGACCAGT
ACTTGTACCGCTTCGTGAGCACAAATAACACTGGCGGAGTCCAGTTCAAC
AAGAACCTGGCCGGGAGATACGCCAACACCTACAAAAACTGGTTCCCGGG
GCCCATGGGCCGAACCCAGGGCTGGAACCTGGGCTCCGGGGTCAACCGCG
CCAGTGTCAGCGCCTTCGCCACGACCAATAGGATGGAGCTCGAGGGCGCG
AGTTACCAGGTGCCCCCGCAGCCGAACGGCATGACCAACAACCTCCAGGG
CAGCAACACCTATGCCCTGGAGAACACTATGATCTTCAACAGCCAGCCGG
CGAACCCGGGCACCACCGCCACGTACCTCGAGGGCAACATGCTCATCACC
AGCGAGAGCGAGACGCAGCCGGTGAACCGCGTGGCGTACAACGTCGGCGG
GCAGATGGCCACCAACAACCAGAGCTCCACCACTGCCCCGCGACCGGCA
CGTACAACCTCCAGGAAATCGTGCCCGGCAGCGTGTGGATGGAGAGGGAC
GTGTACCTCCAAGGACCCATCTGGGCCAAGATCCCAGAGACGGGGGCGCA
CTTTCACCCCTCTCCGGCCATGGGCGGATTCGGACTCAAACACCCACCGC
CCATGATGCTCATCAAGAACACGCCTGTGCCCGGAAATATCACCAGCTTC
TCGGACGTGCCCGTCAGCAGCTTCATCACCCAGTACAGCACCGGGCAGGT
CACCGTGGAGATGGAGTGGGAGCTCAAGAAGGAAAACTCCAAGAGGTGGA
ACCCAGAGATCCAGTACACAAACAACTACAACGACCCCCAGTTTGTGGAC
TTTGCCCCGGACAGCACCGGGGAATACAGAACCACCAGACCTATCGGAAC
GCGTTTCCTTACCCGACCCCTTTAA
```

AAV6 (SEQ ID NO: 6):
ATGGCTGCCGATGGTTATCTTCCAGATTGGCTCGAGGACAACCTCTCTGA

GGGCATTCGCGAGTGGTGGGACTTGAAACCTGGAGCCCCGAAACCCAAAG

CCAACCAGCAAAAGCAGGACGACGGCCGGGGTCTGGTGCTTCCTGGCTAC

AAGTACCTCGGACCCTTCAACGGACTCGACAAGGGGGAGCCCGTCAACGC

GGCGGATGCAGCGGCCCTCGAGCACGACAAGGCCTACGACCAGCAGCTCA

AAGCGGGTGACAATCCGTACCTGCGGTATAACCACGCCGACGCCGAGTTT

CAGGAGCGTCTGCAAGAAGATACGTCTTTTGGGGGCAACCTCGGCGAGC

AGTCTTCCAGGCCAAGAAGAGGGTTCTCGAACCTTTTGGTCTGGTTGAGG

AAGGTGCTAAGACGGCTCCTGGAAAGAAACGTCCGGTAGAGCAGTCGCCA

CAAGAGCCAGACTCCTCCTCGGGCATTGGCAAGACAGGCCAGCAGCCCGC

TAAAAAGAGACTCAATTTTGGTCAGACTGGCGACTCAGAGTCAGTCCCCG

ACCCACAACCTCTCGGAGAACCTCCAGCAACCCCCGCTGCTGTGGGACCT

ACTACAATGGCTTCAGGCGGTGGCGCACCAATGGCAGACAATAACGAAGG

CGCCGACGGAGTGGGTAATGCCTCAGGAAATTGGCATTGCGATTCCACAT

GGCTGGGCGACAGAGTCATCACCACCAGCACCCGAACATGGGCCTTGCCC

ACCTATAACAACCACCTCTACAAGCAAATCTCCAGTGCTTCAACGGGGGC

CAGCAACGACAACCACTACTTCGGCTACAGCACCCCCTGGGGGTATTTTG

ATTTCAACAGATTCCACTGCCATTTCTCACCACGTGACTGGCAGCGACTC

ATCAACAACAATTGGGGATTCCGGCCCAAGAGACTCAACTTCAAGCTCTT

CAACATCCAAGTCAAGGAGGTCACGACGAATGATGGCGTCACGACCATCG

CTAATAACCTTACCAGCACGGTTCAAGTCTTCTCGGACTCGGAGTACCAG

TTGCCGTACGTCCTCGGCTCTGCGCACCAGGGCTGCCTCCCTCCGTTCCC

GGCGGACGTGTTCATGATTCCGCAGTACGGCTACCTAACGCTCAACAATG

GCAGCCAGGCAGTGGGACGGTCATCCTTTTACTGCCTGGAATATTTCCCA

TCGCAGATGCTGAGAACGGGCAATAACTTTACCTTCAGCTACACCTTCGA

GGACGTGCCTTTCCACAGCAGCTACGCGCACAGCCAGAGCCTGGACCGGC

TGATGAATCCTCTCATCGACCAGTACCTGTATTACCTGAACAGAACTCAG

AATCAGTCCGGAAGTGCCCAAAACAAGGACTTGCTGTTTAGCCGGGGGTC

TCCAGCTGGCATGTCTGTTCAGCCCAAAAACTGGCTACCTGGACCCTGTT

ACCGGCAGCAGCGCGTTTCTAAAGTAAAAACAGACAACAACAACAGCAAC

TTTACCTGGACTGGTGCTTCAAAATATAACCTTAATGGGCGTGAATCTAT

AATCAACCCTGGCACTGCTATGGCCTCACACAAAGACGACAAAGACAAGT

TCTTTCCCATGAGCGGTGTCATGATTTTTGGAAAGGAGAGCGCCGGAGCT

TCAAACACTGCATTGGACAATGTCATGATCACAGACGAAGAGGAAATCAA

AGCCACTAACCCCGTGGCCACCGAAAGATTTGGGACTGTGGCAGTCAATC

TCCAGAGCAGCAGCACAGACCCTGCGACCGGAGATGTGCATGTTATGGGA

GCCTTACCTGGAATGGTGTGGCAAGACAGAGACGTATACCTGCAGGGTCC

TATTTGGGCCAAAATTCCTCACACGGATGGACACTTTCACCCGTCTCCTC

TCATGGGCGGCTTTGGACTTAAGCACCCGCCTCCTCAGATCCTCATCAAA

AACACGCCTGTTCCTGCGAATCCTCCGGCAGAGTTTTCGGCTACAAAGTT

TGCTTCATTCATCACCCAGTATTCCACAGGACAAGTGAGCGTGGAGATTG

AATGGGAGCTGCAGAAAGAAAACAGCAAACGCTGGAATCCCGAAGTGCAG

TATACATCTAACTTTGCCAAATCTGCCAACGTTGATTTCACTGTGGACAA

CAATGGACTTTATACTGAGCCTCGCCCCATTGGCACACGTTTCCTCACCC

GTCCCCTGTAA

Therapeutic Uses

Another aspect of the disclosure pertains to uses of the rAAV nucleic acid vectors and rAAV particles described herein for efficient transduction of cells, tissues, and/or organs of interest, and/or for use in gene therapy.

In some embodiments, the disclosure provides a method for transduction of cells, tissues, and/or organs of interest, comprising introducing into a cell, a composition comprising an effective amount of a rAAV particle described herein, such as an rAAV particle comprising a rAAV nucleic acid vector described herein.

In certain embodiments, the rAAV nucleic acid vectors and rAAV particles described herein are used for transduction of mammalian host cells, including for example, human, primate, murine, feline, canine, porcine, ovine, bovine, equine, epine, caprine and lupine host cells. In certain embodiments, the rAAV nucleic acid vectors and rAAV particles described herein are used for transduction of endothelial, epithelial, vascular, liver, lung, heart, pancreas, intestinal, kidney, muscle, bone, dendritic, cardiac, neural, blood, brain, fibroblast or cancer cells. In some embodiments, the rAAV particles comprising a modified AAV1 capsid described herein (e.g., Y705F+Y731F+T492V) are used for transducing muscle (e.g., mouse muscle). In some embodiments, the rAAV particles comprising a modified AAV5 capsid described herein (e.g., Y436F+Y693F+Y719F) are used for transducing retinal cells (e.g., mouse cells) or airway epithelial cells (e.g., human cells). In some embodiments, the rAAV particles comprising a modified AAV6 capsid described herein (e.g., Y705F+Y731F+T492V) are used for transducing hematopoietic stem cells (e.g., human cells), dendritic cells (e.g., human cells), monocytes (e.g., human cells), airway epithelial cells (e.g., human cells), muscle (e.g., mouse or dog muscle), liver (e.g., mouse liver), pancreas (e.g., mouse pancreas), or microglial cells (e.g., mouse cells).

In one embodiment, cells, tissues, and/or organs of a subject are transduced using the rAAV particles described herein.

The term "subject," as used herein, describes an organism, including mammals such as primates, to which treatment with the compositions according to the present disclosure can be provided. Mammalian species that can benefit from the disclosed methods of treatment include, but are not limited to, humans; apes; chimpanzees; orangutans; monkeys; domesticated animals such as dogs and cats; livestock such as horses, cattle, pigs, sheep, goats, and chickens; and other animals such as mice, rats, guinea pigs, and hamsters.

In some embodiments, the disclosure provides a method for treatment of a disease, wherein the method comprises administering, to a subject in need of such treatment, an effective amount of a composition comprising the rAAV particle described herein.

The term "treatment" or any grammatical variation thereof (e.g., treat, treating, and treatment, etc.), as used herein, includes but is not limited to, alleviating a symptom of a disease or condition; and/or reducing, suppressing, inhibiting, lessening, ameliorating or affecting the progression, and/or severity of a disease or condition.

The term "effective amount," as used herein, refers to an amount that is capable of treating a disease or condition or otherwise capable of producing an intended therapeutic effect (e.g., transduction of a cell or tissue or organ).

The disclosure also provides for the use of a composition disclosed herein in the manufacture of a medicament for treating, preventing or ameliorating the symptoms of a disease, disorder, dysfunction, injury or trauma, including, but not limited to, the treatment, prevention, and/or prophylaxis of a disease, disorder or dysfunction, and/or the amelioration of one or more symptoms of such a disease, disorder or dysfunction. Exemplary conditions for which rAAV viral based gene therapy may find particular utility include, but are not limited to, cancer, diabetes, autoimmune disease, kidney disease, cardiovascular disease, pancreatic disease, intestinal disease, liver disease, neurological disease, neuromuscular disorder, neuromotor deficit, neuroskeletal impairment, neurological disability, neurosensory dysfunction, stroke, alpha-1-antitrypsin (AAT) deficiency, Batten's disease, ischemia, an eating disorder, Alzheimer's disease, Huntington's disease, Parkinson's disease, skeletal disease and pulmonary disease.

In some embodiments, a composition comprising an rAAV particle comprising a modified AAV1 capsid protein as described herein (e.g., a modified AAV1 capsid protein comprising replacement of tyrosine residues with non-tyrosine residues and a replacement of a threonine residue with a non-threonine residue at each of the positions corresponding to Y705, Y731, and T492 of the wild-type AAV1 capsid protein having the sequence of SEQ ID NO: 1) is used in a method of manufacturing a medicament for treating, preventing or ameliorating one or more symptoms of muscular dystrophy or alpha-1-antitripsin deficiency.

In some embodiments, a composition comprising an rAAV particle comprising a modified AAV5 capsid protein as described herein (e.g., a modified AAV5 capsid protein comprising replacement of tyrosine residues with non-tyrosine residues at each of the positions corresponding to Y436, Y693, and Y719 of a wild-type AAV5 capsid protein having the sequence of SEQ ID NO: 2) is used in a method of manufacturing a medicament for treating, preventing or ameliorating one or more symptoms of retinitis pigmentosa, age-related macular degeneration, or cystic fibrosis.

In some embodiments, a composition comprising an rAAV particle comprising a modified AAV6 capsid protein as described herein (e.g., a modified AAV6 capsid protein comprising replacement of tyrosine residues with non-tyrosine residues and a replacement of a threonine residue with a non-threonine residue at each of the positions corresponding to Y705, Y731, and T492 of a wild-type AAV6 capsid protein having the sequence of SEQ ID NO: 3) is used in a method of manufacturing a medicament for treating, preventing or ameliorating one or more symptoms of an immune disease that involves treatment with genetically-modified dendritic cells and/or macrophages, breast cancer, prostate cancer, pancreatic cancer, Alzheimer's disease, sickle cell disease, beta-thalassemia, or cardiovascular disease.

The disclosure also provides a method for treating or ameliorating the symptoms of such a disease, injury, disorder, or dysfunction in a mammal. Such methods generally involve at least the step of administering to a mammal in need thereof, one or more of the rAAV particles described herein, in an amount and for a time sufficient to treat or ameliorate the symptoms of such a disease, injury, disorder, or dysfunction in the mammal.

In some embodiments, a composition comprising an rAAV particle comprising a modified AAV1 capsid protein as described herein (e.g., a modified AAV1 capsid protein comprising replacement of tyrosine residues with non-tyrosine residues and a replacement of a threonine residue with a non-threonine residue at each of the positions corresponding to Y705, Y731, and T492 of the wild-type AAV1 capsid protein having the sequence of SEQ ID NO: 1) is used in a method of treating, preventing or ameliorating one or more symptoms of muscular dystrophy or alpha-1-antitripsin deficiency.

In some embodiments, a composition comprising an rAAV particle comprising a modified AAV5 capsid protein as described herein (e.g., a modified AAV5 capsid protein comprising replacement of tyrosine residues with non-tyrosine residues at each of the positions corresponding to Y436, Y693, and Y719 of a wild-type AAV5 capsid protein having the sequence of SEQ ID NO: 2) is used in a method of treating, preventing or ameliorating one or more symptoms of retinitis pigmentosa, age-related macular degeneration, or cystic fibrosis.

In some embodiments, a composition comprising an rAAV particle comprising a modified AAV6 capsid protein as described herein (e.g., a modified AAV6 capsid protein comprising replacement of tyrosine residues with non-tyrosine residues and a replacement of a threonine residue with a non-threonine residue at each of the positions corresponding to Y705, Y731, and T492 of a wild-type AAV6 capsid protein having the sequence of SEQ ID NO: 3) is used in a method of treating, preventing or ameliorating one or more symptoms of an immune disease that involves treatment with genetically-modified dendritic cells and/or macrophages, breast cancer, prostate cancer, pancreatic cancer, Alzheimer's disease, sickle cell disease, beta-thalassemia, or cardiovascular disease. In some embodiments, a composition comprising an rAAV particle comprising a modified AAV6 capsid protein as described herein is used in a method of targeting blood cells, blood stem cells, blood progenitor cells, dendritic cells, macrophages, and/or blood differentiated cells, or a combination thereof.

Such treatment regimens are particularly contemplated in human therapy, via administration of one or more compositions either intramuscularly, intravenously, subcutaneously, intrathecally, intraperitoneally, or by direct injection into an organ or a tissue of the subject under care, such as injection into the eye.

The disclosure also provides a method for providing to a mammal in need thereof, a therapeutically-effective amount of the rAAV compositions of the present disclosure, in an amount, and for a time effective to provide the patient with a therapeutically-effective amount of the desired therapeutic agent(s) encoded by one or more nucleic acid segments comprised within the rAAV vector. Preferably, the therapeutic agent is selected from the group consisting of a polypeptide, a peptide, an antibody, an antigen binding fragment, a ribozyme, a peptide nucleic acid, a siRNA, an RNAi, an antisense oligonucleotide and an antisense polynucleotide.

Pharmaceutical Compositions

The present disclosure also provides therapeutic or pharmaceutical compositions comprising the active ingredient, such as a rAAV particle described herein, in a form that can be combined with a therapeutically or pharmaceutically acceptable carrier. The rAAV particles may be prepared in a variety of compositions, and may also be formulated in appropriate pharmaceutical vehicles for administration to human or animal subjects.

The rAAV particles described herein and compositions comprising them provide new and useful therapeutics for the treatment, control, and amelioration of symptoms of a variety of disorders.

The disclosure also provides compositions comprising one or more of the disclosed nucleic acid molecules, rAAV nucleic acid vectors, rAAV particles, or mammalian cells. As described herein, such compositions may further comprise a pharmaceutical excipient, buffer, or diluent, and may be formulated for administration to an animal, and particularly a human being. Such compositions may further optionally comprise a liposome, a lipid, a lipid complex, a microsphere, a microparticle, a nanosphere, or a nanoparticle, or may be otherwise formulated for administration to the cells, tissues, organs, or body of a subject in need thereof. Such compositions may be formulated for use in a variety of therapies, such as for example, in the amelioration, prevention, and/or treatment of conditions such as peptide deficiency, polypeptide deficiency, peptide overexpression, polypeptide overexpression, including for example, conditions which result in diseases or disorders such as cancers, tumors, or other malignant growths, neurological deficit dysfunction, autoimmune diseases, articular diseases, cardiac or pulmonary diseases, ischemia, stroke, cerebrovascular accidents, transient ischemic attacks (TIA); diabetes and/or other diseases of the pancreas; cardiocirculatory disease or dysfunction (including, e.g., hypotension, hypertension, atherosclerosis, hypercholesterolemia, vascular damage or disease; neural diseases (including, e.g., Alzheimer's, Huntington's, Tay-Sach's and Parkinson's disease, memory loss, trauma, motor impairment, neuropathy, and related disorders); biliary, renal or hepatic disease or dysfunction; musculoskeletal or neuromuscular diseases (including, e.g., arthritis, palsy, cystic fibrosis (CF), amyotrophic lateral sclerosis (ALS), multiple sclerosis (MS), muscular dystrophy (MD), and such like).

In some embodiments, the rAAV particles may be administered to a subject at concentrations ranging from $10^6$ to $10^{14}$ particles/ml or $10^3$ to $10^{13}$ particles/ml, or any values therebetween for either range, such as for example, about $10^6$, $10^7$, $10^8$, $10^9$, $10^{10}$, $10^{11}$, $10^{12}$, $10^{13}$, or $10^{14}$ particles/ml. In one embodiment, rAAV particles of higher than $10^{13}$ particles/ml are to be administered. In some embodiments, rAAV particles may be administered to a subject at concentrations ranging from $10^6$ to $10^{14}$ vector genomes(vgs)/ml or $10^3$ to $10^{15}$ vgs/ml, or any values therebetween for either range, such as for example, about $10^6$, $10^7$, $10^8$, $10^9$, $10^{10}$, $10^{11}$, $10^{12}$, $10^{13}$, or $10^{14}$ vgs/ml. In one embodiment, rAAV particles of higher than $10^{13}$ vgs/ml are to be administered. The rAAV particles can be administered as a single dose, or divided into two or more administrations as may be required to achieve therapy of the particular disease or disorder being treated. In some embodiments, 0.0001 ml to 10 mls are delivered to a subject.

In some embodiments of rAAV-based gene therapy regimens, a lower titer of infectious particles can be used when using the modified-capsid rAAV particles, than compared to conventional gene therapy protocols.

In certain embodiments, the disclosure provides formulations of one or more rAAV-based compositions disclosed herein in pharmaceutically acceptable solutions for administration to a cell or an animal, either alone or in combination with one or more other modalities of therapy, and in particular, for therapy of human cells, tissues, and diseases affecting man.

If desired, nucleic acid segments, RNA, DNA or PNA compositions that express one or more of therapeutic gene products may be administered in combination with other agents as well, such as, e.g., proteins or polypeptides or various pharmaceutically-active agents, including one or more systemic or topical administrations of therapeutic polypeptides, biologically active fragments, or variants thereof. In fact, there is virtually no limit to other components that may also be included, given that the additional agents do not cause a significant adverse effect upon contact with the target cells or host tissues. The rAAV particles may thus be delivered along with various other agents as required in the particular instance. Such compositions may be purified from host cells or other biological sources, or alternatively may be chemically synthesized as described herein. Likewise, such compositions may further comprise substituted or derivatized RNA, DNA, siRNA, mRNA, tRNA, ribozyme, catalytic RNA molecules, or PNA compositions and such like.

Formulation of pharmaceutically-acceptable excipients and carrier solutions is well-known to those of skill in the art, as is the development of suitable dosing and treatment regimens for using the particular compositions described herein in a variety of treatment regimens, including e.g., oral, parenteral, intravenous, intranasal, intra-articular, intramuscular administration and formulation.

Typically, these formulations may contain at least about 0.1% of the active compound or more, although the percentage of the active ingredient(s) may, of course, be varied and may conveniently be between about 1 or 2% and about 70% or 80% or more of the weight or volume of the total formulation. Naturally, the amount of active compound(s) in each therapeutically-useful composition may be prepared is such a way that a suitable dosage will be obtained in any given unit dose of the compound. Factors such as solubility, bioavailability, biological half-life, route of administration, product shelf life, as well as other pharmacological considerations will be contemplated by one skilled in the art of preparing such pharmaceutical formulations, and as such, a variety of dosages and treatment regimens may be desirable.

In certain circumstances it will be desirable to deliver the rAAV particles in suitably formulated pharmaceutical compositions disclosed herein either subcutaneously, intraocularly, intravitreally, parenterally, subcutaneously, intravenously, intracerebro-ventricularly, intramuscularly, intrathecally, orally, intraperitoneally, by oral or nasal inhalation, or by direct injection to one or more cells, tissues, or organs by direct injection. The methods of administration may also include those modalities as described in U.S. Pat. Nos. 5,543,158, 5,641,515 and/or 5,399,363 (each of which is specifically incorporated herein in its entirety by express reference thereto). Solutions of the active compounds as freebase or pharmacologically acceptable salts may be prepared in sterile water and may also suitably mixed with one or more surfactants, such as hydroxypropylcellulose. Dispersions may also be prepared in glycerol, liquid polyethylene glycols, and mixtures thereof and in oils. Under ordinary conditions of storage and use, these preparations contain a preservative to prevent the growth of microorganisms.

The pharmaceutical forms of the rAAV particle compositions suitable for injectable use include sterile aqueous solutions or dispersions and sterile powders for the extemporaneous preparation of sterile injectable solutions or dispersions (U.S. Pat. No. 5,466,468, specifically incorporated herein in its entirety by express reference thereto). In all cases the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, saline, ethanol, polyol (e.g., glycerol, propylene glycol, and liquid polyethylene glycol, and the like), suitable mixtures thereof, and/or vegetable oils. Proper fluidity may be maintained, for example, by the use of a coating, such as lecithin, by the maintenance of the required particle size in the case of dispersion and by the use of surfactants.

The term "carrier" refers to a diluent, adjuvant, excipient, or vehicle with which the compound is administered. Such pharmaceutical carriers can be sterile liquids, such as water and oils, including those of petroleum oil such as mineral oil, vegetable oil such as peanut oil, soybean oil, and sesame oil, animal oil, or oil of synthetic origin. Saline solutions and aqueous dextrose and glycerol solutions can also be employed as liquid carriers.

The compositions of the present disclosure can be administered to the subject being treated by standard routes including, but not limited to, pulmonary, intranasal, oral, inhalation, parenteral such as intravenous, topical, transdermal, intradermal, transmucosal, intraperitoneal, intramuscular, intracapsular, intraorbital, intravitreal, intracardiac, transtracheal, subcutaneous, subcuticular, intraarticular, subcapsular, subarachnoid, intraspinal, epidural and intrasternal injection.

For administration of an injectable aqueous solution, for example, the solution may be suitably buffered, if necessary, and the liquid diluent first rendered isotonic with sufficient saline or glucose. These particular aqueous solutions are especially suitable for intravenous, intramuscular, intravitreal, subcutaneous and intraperitoneal administration. In this connection, a sterile aqueous medium that can be employed will be known to those of skill in the art in light of the present disclosure. For example, one dosage may be dissolved in 1 mL of isotonic NaCl solution and either added to 1000 mL of hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, and the general safety and purity standards as required by, e.g., FDA Office of Biologics standards.

Sterile injectable solutions are prepared by incorporating the rAAV particles in the required amount in the appropriate solvent with several of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

The rAAV particle compositions disclosed herein may also be formulated in a neutral or salt form. Pharmaceutically-acceptable salts include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like. Upon formulation, solutions will be administered in a manner compatible with the dosage formulation and in such amount as is therapeutically effective. The formulations are easily administered in a variety of dosage forms such as injectable solutions, drug-release capsules, and the like.

The amount of rAAV particle compositions and time of administration of such compositions will be within the purview of the skilled artisan having benefit of the present teachings. It is likely, however, that the administration of therapeutically-effective amounts of the disclosed compositions may be achieved by a single administration, such as for example, a single injection of sufficient numbers of infectious particles to provide therapeutic benefit to the patient undergoing such treatment. Alternatively, in some circumstances, it may be desirable to provide multiple, or successive administrations of the rAAV particle compositions, either over a relatively short, or a relatively prolonged period of time, as may be determined by the medical practitioner overseeing the administration of such compositions.

The composition may include rAAV particles, either alone, or in combination with one or more additional active ingredients, which may be obtained from natural or recombinant sources or chemically synthesized.

Expression Vectors

The present disclosure contemplates a variety of AAV-based expression systems, and nucleic acid vectors. In one embodiment the preferred AAV expression vectors comprise at least a first nucleic acid segment that encodes a therapeutic peptide, protein, or polypeptide. In another embodiment, the preferred AAV expression vectors disclosed herein comprise at least a first nucleic acid segment that encodes an antisense molecule. In another embodiment, a promoter is operatively linked to a sequence region that encodes a functional mRNA, a tRNA, a ribozyme or an antisense RNA.

The choice of which expression vector and ultimately to which promoter a polypeptide coding region is operatively linked depends directly on the functional properties desired, e.g., the location and timing of protein expression, and the host cell to be transformed. These are well known limitations inherent in the art of constructing recombinant DNA molecules. However, a vector useful in practicing the present disclosure is capable of directing the expression of the functional RNA to which it is operatively linked.

A variety of methods have been developed to operatively link DNA to vectors via complementary cohesive termini or blunt ends. For instance, complementary homopolymer tracts can be added to the DNA segment to be inserted and to the vector DNA. The vector and DNA segment are then joined by hydrogen bonding between the complementary homopolymeric tails to form recombinant DNA molecules.

To express a therapeutic agent in accordance with the present disclosure one may prepare a rAAV particle comprising a rAAV nucleic acid vector that comprises a therapeutic agent-encoding nucleic acid segment under the control of one or more promoters. To bring a sequence "under the control of" a promoter, one positions the 5' end of the transcription initiation site of the transcriptional reading frame generally between about 1 and about 50 nucleotides "downstream" of (i.e., 3' of) the chosen promoter. The "upstream" promoter stimulates transcription of the DNA and promotes expression of the encoded polypeptide. This is the meaning of "recombinant expression" in this context. Particularly preferred recombinant vector constructs are those that comprise a rAAV nucleic acid vector. Such vectors are described in detail herein.

When the use of such nucleic acid vectors is contemplated for introduction of one or more exogenous proteins, polypeptides, peptides, ribozymes, and/or antisense oligonucleotides, to a particular cell transfected with the nucleic acid vector, one may employ the rAAV nucleic acid vectors disclosed herein by genetically modifying the vectors to further comprise at least a first exogenous polynucleotide operably positioned downstream and under the control of at least a first heterologous promoter that expresses the polynucleotide in a cell comprising the vector to produce the encoded peptide, protein, polypeptide, ribozyme, siRNA, RNAi or antisense oligonucleotide. Such constructs may employ heterologous promoters that are constitutive, inducible, or even cell-specific promoters. Exemplary such promoters include, but are not limited to, viral, mammalian, and avian promoters, including for example a CMV promoter, a beta-actin promoter, a hybrid CMV promoter, a hybrid beta-actin promoter, an EF1 promoter, a U1a promoter, a U1b promoter, a Tet-inducible promoter, a VP16-LexA promoter, and such like.

The nucleic acid vectors or expression systems may also further comprise one or more enhancers, regulatory elements, transcriptional elements, to alter or effect transcription of the heterologous gene cloned in the rAAV vectors. For example, the rAAV vectors of the present disclosure may further comprise at least a first CMV enhancer, a synthetic enhancer, or a cell- or tissue-specific enhancer. The exogenous polynucleotide may also further comprise one or more intron sequences.

Therapeutic Kits

The disclosure also encompasses kits comprising one or more of the rAAV particles, nucleic acid vectors, proteins, host cells, and/or compositions described herein together with one or more pharmaceutically-acceptable excipients, carriers, diluents, adjuvants, and/or other components, as may be employed in the formulation of particular delivery formulations, and in the preparation of therapeutic agents for administration to a subject, and in particularly, to a human. In particular, such kits may comprise one or more of the disclosed rAAV particle compositions in combination with instructions for using the composition in the treatment of such disorders in a subject, and may typically further include containers prepared for convenient commercial packaging.

Therapeutic kits may also be prepared that comprise at least one of the compositions disclosed herein and instructions for using the composition as a therapeutic agent. The container means for such kits may typically comprise at least one vial, test tube, flask, bottle, syringe or other container means, into which the disclosed rAAV particle composition(s) may be placed, and preferably suitably aliquoted. Where a second therapeutic polypeptide composition is also provided, the kit may also contain a second distinct container means into which this second composition may be placed. Alternatively, the plurality of therapeutic biologically active compositions may be prepared in a single pharmaceutical composition, and may be packaged in a single container means, such as a vial, flask, syringe, bottle, or other suitable single container means. The kits of the present disclosure will also typically include a means for containing the vial(s) in close confinement for commercial sale, such as, e.g., injection or blow-molded plastic containers into which the desired vial(s) are retained.

AAV Capsid Proteins

Supramolecular assembly of approximately 60 individual capsid protein subunits into a non-enveloped, T-1 icosahedral lattice capable of protecting the AAV DNA genome is a critical step in the life-cycle of the helper-dependent human parvovirus, adeno-associated virus (AAV), such as AAV2. The mature 20-nm diameter AAV2 particle is composed of three structural proteins designated VP1, VP2, and VP3 (molecular masses of 87, 73, and 62 kDa respectively) in a ratio of 1:1:18. Based on its symmetry and these molecular weight estimates, of the 60 capsid proteins comprising the particle, three are VP1 proteins, three are VP2 proteins, and fifty-four are VP3 proteins.

Biological Functional Equivalents

Also provided herein are modifications to the structure of the AAV capsid proteins as described herein to obtain functional rAAV particles that possess desirable characteristics, particularly with respect to improved delivery of therapeutic gene constructs to selected mammalian cell, tissues, and organs for the treatment, prevention, and prophylaxis of various diseases and disorders, as well as means for the amelioration of symptoms of such diseases, and to facilitate the expression of exogenous therapeutic and/or prophylactic polypeptides of interest via rAAV vector-mediated gene therapy. As mentioned above, one of the key aspects of the disclosure is the introduction of modifications into specific capsid protein sequences to produce modified vectors with improved properties for effecting gene therapy in mammalian systems.

For example, certain amino acids may be substituted for other amino acids in a protein structure without appreciable loss of interactive binding capacity with structures such as, for example, antigen-binding regions of antibodies or binding sites on substrate molecules. Since it is the interactive capacity and nature of a protein that defines that protein's biological functional activity, certain amino acid sequence substitutions can be made in a protein sequence, and, of course, its underlying DNA coding sequence, and nevertheless obtain a protein with like properties. It is thus contemplated herein that various changes may be made in the polynucleotide or polypeptide sequences disclosed herein, without appreciable loss of their biological utility or activity.

In making such changes, the hydropathic index of amino acids may be considered. The importance of the hydropathic amino acid index in conferring interactive biologic function on a protein is generally understood in the art (Kyte and Doolittle, 1982, incorporated herein by reference). It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like. Each amino acid has been assigned a hydropathic index on the basis of their hydrophobicity and charge characteristics (Kyte and Doolittle, 1982), these are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

Exemplary Definitions

In accordance with the present disclosure, polynucleotides, nucleic acid segments, nucleic acid sequences, and the like, include, but are not limited to, DNAs (including and not limited to genomic DNAs), genes, peptide nucleic acids (PNAs), RNAs (including, but not limited to, rRNAs, mRNAs, miRNAs and tRNAs), nucleosides, and suitable nucleic acid segments either obtained from natural sources, chemically synthesized, modified, or otherwise prepared or synthesized in whole or in part by the hand of man.

Unless defined otherwise, all technical and scientific terms used herein have the same meaning as commonly understood by one of ordinary skill in the art to which this disclosure pertains. Although any methods and compositions similar or equivalent to those described herein can be used in the practice or testing of the present disclosure, the preferred methods and compositions are described herein. For purposes of the present disclosure, the following terms are defined below:

The term "promoter," as used herein refers to a region or regions of a nucleic acid sequence that regulates transcription.

The term "regulatory element," as used herein, refers to a region or regions of a nucleic acid sequence that regulates transcription. Exemplary regulatory elements include, but are not limited to, enhancers, post-transcriptional elements, transcriptional control sequences, and such like.

The term "vector," as used herein, refers to a nucleic acid molecule (typically comprised of DNA) capable of replication in a host cell and/or to which another nucleic acid segment can be operatively linked so as to bring about replication of the attached segment. A plasmid, cosmid, or a viral genome is an exemplary vector.

The term "substantially corresponds to," "substantially homologous," or "substantial identity," as used herein, denote a characteristic of a nucleic acid or an amino acid sequence, wherein a selected nucleic acid or amino acid sequence has at least about 70 or about 75 percent sequence identity as compared to a selected reference nucleic acid or amino acid sequence. More typically, the selected sequence and the reference sequence will have at least about 76, 77, 78, 79, 80, 81, 82, 83, 84 or even 85 percent sequence identity, and more preferably at least about 86, 87, 88, 89, 90, 91, 92, 93, 94, or 95 percent sequence identity. More preferably still, highly homologous sequences often share greater than at least about 96, 97, 98, or 99 percent sequence identity between the selected sequence and the reference sequence to which it was compared.

The percentage of sequence identity may be calculated over the entire length of the sequences to be compared, or may be calculated by excluding small deletions or additions which total less than about 25 percent or so of the chosen reference sequence. The reference sequence may be a subset of a larger sequence, such as a portion of a gene or flanking sequence, or a repetitive portion of a chromosome. However, in the case of sequence homology of two or more polynucleotide sequences, the reference sequence will typically comprise at least about 18-25 nucleotides, more typically at least about 26 to 35 nucleotides, and even more typically at least about 40, 50, 60, 70, 80, 90, or even 100 or so nucleotides.

Desirably, which highly homologous fragments are desired, the extent of percent identity between the two sequences will be at least about 80%, preferably at least about 85%, and more preferably about 90% or 95% or higher, as readily determined by one or more of the sequence comparison algorithms well-known to those of skill in the art, such as e.g., the FASTA program analysis described by Pearson and Lipman (Proc. Natl. Acad. Sci. USA, 85(8): 2444-8, April 1988).

The term "operably linked" or "operatively linked," as used herein, refers to that the nucleic acid sequences being linked are typically contiguous, or substantially contiguous, and, where necessary to join two protein coding regions, contiguous and in reading frame. However, since enhancers generally function when separated from the promoter by several kilobases and intronic sequences may be of variable lengths, some polynucleotide elements may be operably linked but not contiguous.

Without further elaboration, it is believed that one skilled in the art can, based on the above description, utilize the present disclosure to its fullest extent. The following specific embodiments are, therefore, to be construed as merely illustrative, and not limitative of the remainder of the disclosure in any way whatsoever. All publications cited herein are incorporated by reference for the purposes or subject matter referenced herein.

EXAMPLES

Example 1

AAV1, AAV5, and AAV6 Capsid Mutants Have Enhanced Transgene Expression Levels

Specific AAV1, AAV5, AAV6 capsid mutants were tested for transduction efficiency. The mutants tested are shown in the table below. Exemplary tissues/organs for use with each serotype are also shown.

| Serotypes | Mutations | Exemplary Tissues/Organs |
| --- | --- | --- |
| AAV1 | Y705F + Y731F + T492V | Muscle (mouse) |
| AAV5 | Y436F + Y693F + Y719F | Retina (mouse) Airway epithelial cells (human) |
| AAV6 | Y705F + Y731F + T492V | Hematopoietic stem cells, dendritic cells, monocytes, airway epithelial cells (human) Muscle (mouse, dog) Microglial cells, pancreas, liver (mouse) |

Transduction Efficiency of WT and Various Capsid-Modified AAV1 Serotype Vectors in a Murine Muscle Cell Line In Vitro [C2C12] and in Murine Muscles In Vivo Wild-type (WT) and mutant AAV1 vectors carrying a nucleic acid encoding GFP or Alpha-1 antitrypsin (AAT) were produced using standard methods and efficiency of each vector was evaluated in vitro and in vivo.

For in vitro analysis, EGFP expression levels was measured at 48 h post-infection following transduction at an MOI (multiplicity of infection) of $1\times10^3$ vgs/cell using C2C12 cells. EGFP transgene expression was assessed as the total area of green fluorescence ($pixel^2$) per visual field (mean±SD).

For in vivo analysis, AAT expression levels were measured in muscle by ELISA following intramuscular injection of WT (AAV1) and mutant Y705−731F+T492V mutant AAV1 vectors (AAV1m) in C57BL6/J mice.

Figure 1B:
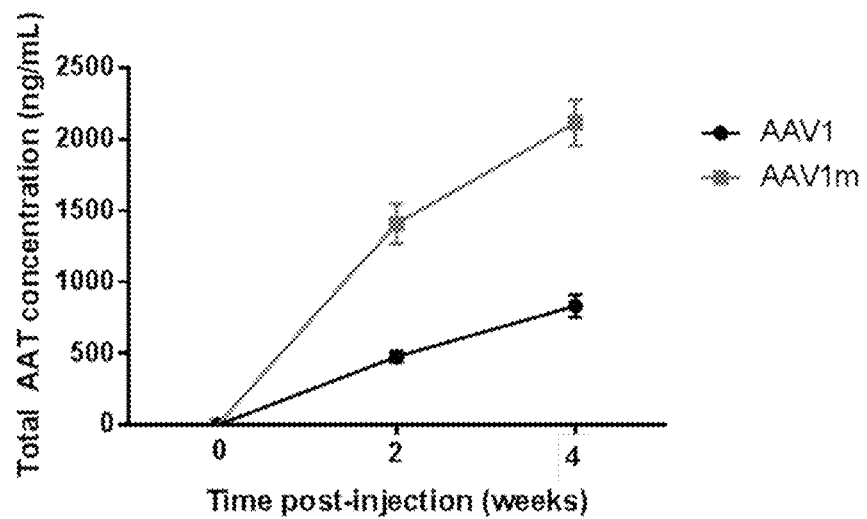
FIG. 1B is a graph showing the total Alpha-1 antitrypsin (AAT) concentration in muscle from mice injected with wild-type AAV1 vectors or mutant AAV1 Y705F+Y731F+T492V vector (AAV1m).

The transduction efficiency of the AAV1 Y705F+Y731F+T492V vector was significantly higher than that of the wild-type vector both in vitro in C2C12 muscle cells (FIG. 1A) and in vivo in mouse muscle (FIG. 1B).

Imaging of Major Organs for GFP Expression Following Intraperitoneal Injection of Various Mutant scAAV6 Vectors in Mice In Vivo WT and mutant AAV6 vectors carrying a nucleic acid encoding mCherry were produced using standard methods and efficiency of each vector was evaluated in vivo.

mCherry expression analysis of different mice organs was performed following i.p. injection of $10^{11}$ vgs of WT and mutant AAV6 vectors. Organs were harvested two weeks post-injection and analyzed using a UVP Biolmaging System.

Figure 2:
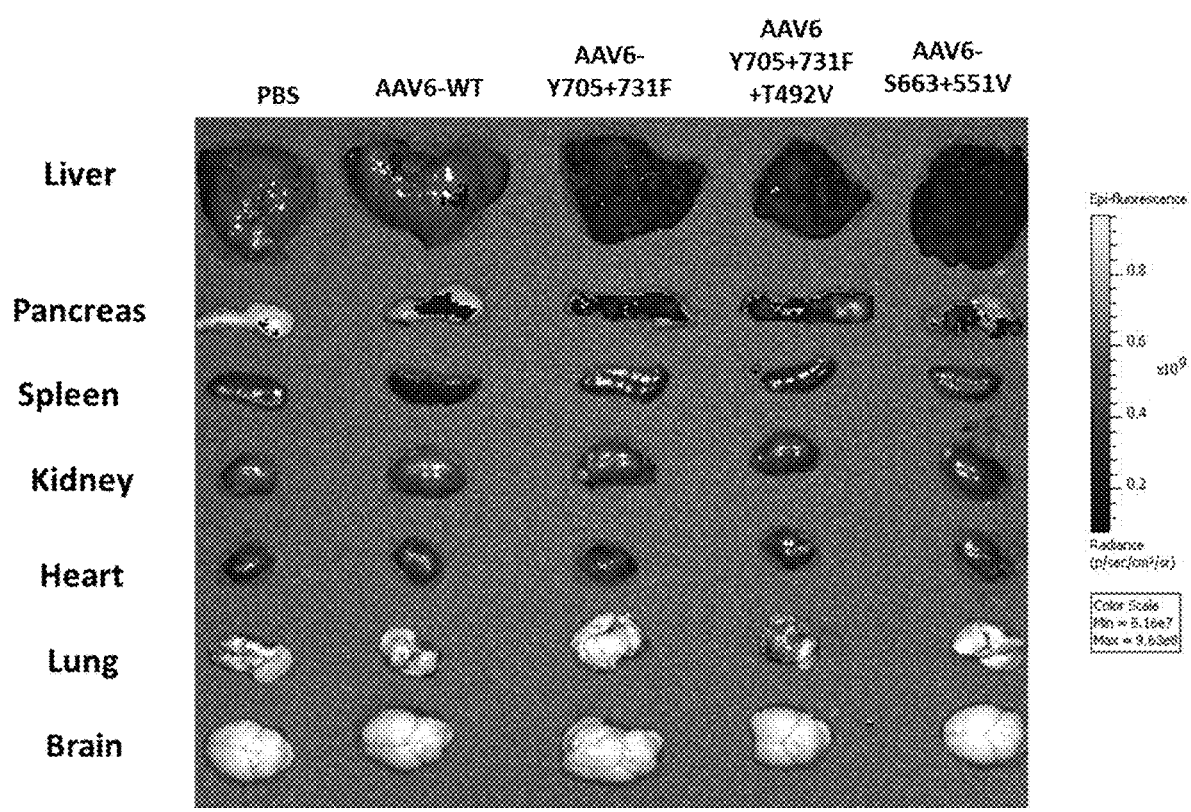
FIG. 2 is a photograph showing mCherry expression in major organs of mice following injection of wild-type (WT) or mutant AAV6 vectors.

The transduction efficiency of the AAV6 Y705F+Y731F+T492V was significantly higher than the wild-type vector in the liver and pancreas (FIG. 2).

Transduction Efficiency of WT and Various Mutant scAAV6 Vectors in Mouse Pancreas In Vivo WT and mutant AAV6 vectors carrying a nucleic acid encoding EGFP were produced using standard methods and efficiency of each vector was evaluated in vivo.

Mice pancreas were harvested two weeks post-injection of $10^{11}$ vgs of WT and mutant-AAV6 vectors and analyzed for EGFP expression. DAPI and anti-insulin antibodies were used for nuclear and cytoplasmic staining.

Figure 3:
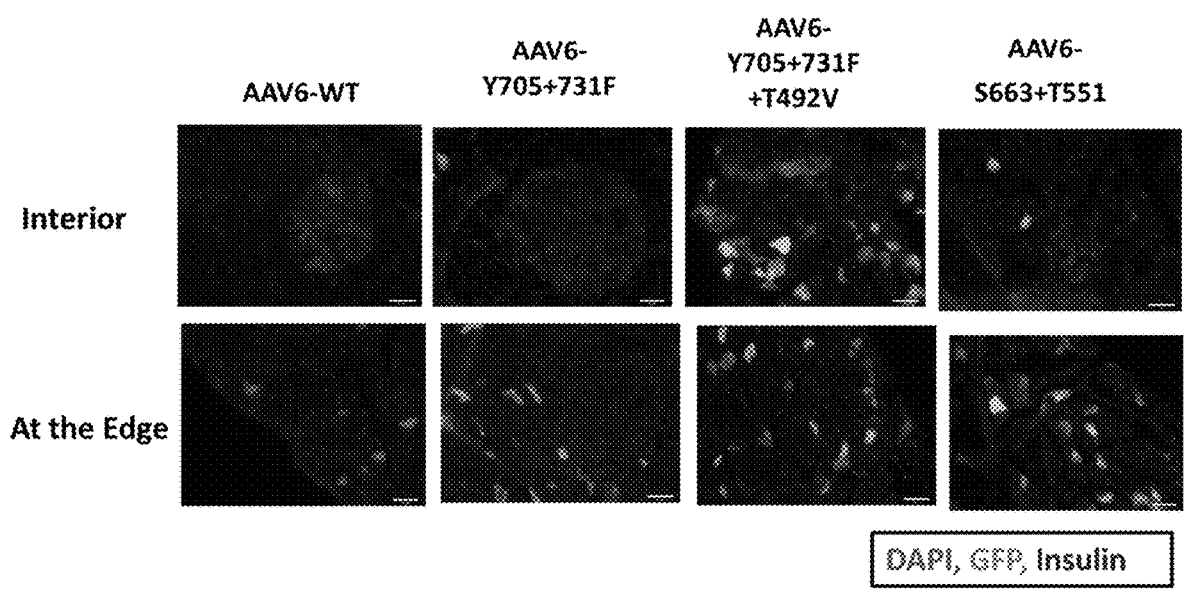
FIG. 3 is a series of photographs showing EGFP expression in mouse pancreas at the interior or edge following injection with wild-type (WT) or mutant AAV6 vectors.

The transduction efficiency of the AAV6 Y705F+Y731F+T492V was significantly higher than the wild-type vector in pancreas, both at the edge of the organ and in the interior (FIG. 3).

Transduction Efficiency of WT and Mutant scAAV6 Vectors in Primary Murine Glial Cells In Vivo WT and mutant AAV6 vectors carrying a nucleic acid encoding EGFP were produced using standard methods and efficiency of each vector was evaluated in vivo.

Mice brains were harvested two weeks post-injection of $1 \times 10^{10}$ vgs of WT and mutant-AAV6 vectors expressing EGFP. Primary cells were cultured and the EGFP expression level was analyzed by flourescence microscopy. Anti-CD11B antibodies were used to identify glial cells.

Figure 4:
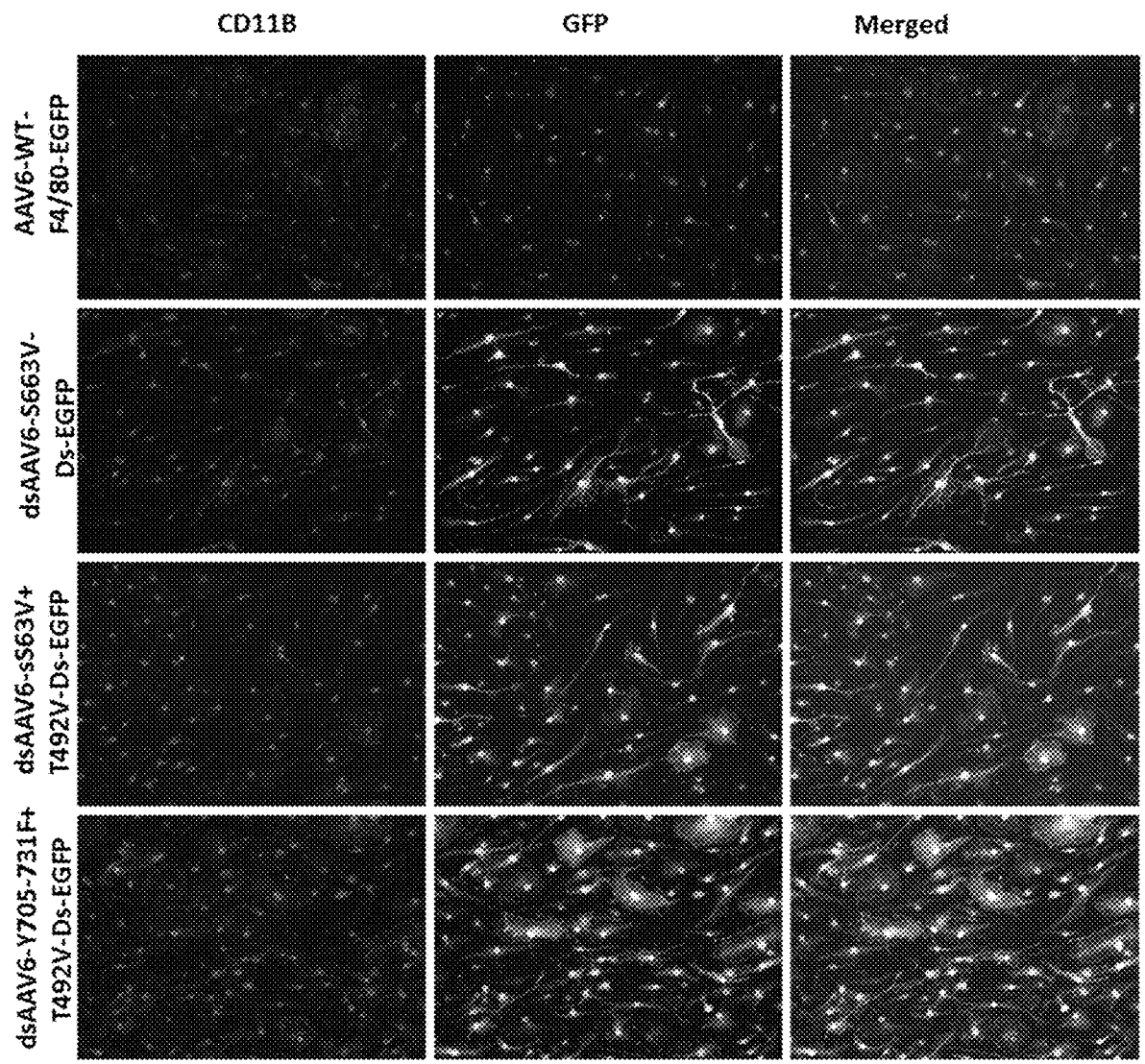
FIG. 4 is a series of photographs showing EGFP expression in primary murine glial cells cultured from mice injected with wild-type (WT) or mutant AAV6 vectors.

The transduction efficiency of the AAV6 Y705F+Y731F+T492V was significantly higher than the wild-type vector in glial cells (FIG. 4).

Transduction Efficiency of Y705+731F+T492V Mutant scAAV6 Vectors in Microglial Cells in Injected Brains in Mice In Vivo WT and mutant AAV6 vectors carrying a nucleic acid encoding EGFP were produced using standard methods and efficiency of each vector was evaluated in vivo.

Mice brains were harvested two weeks post-injection of $1 \times 10^{10}$ vgs of WT and mutant-AAV6 vectors expressing EGFP. Microglia/macrophage-specific marker anti-IBA antibodies were used to identify EGFP positive glial cells.

Figure 5:
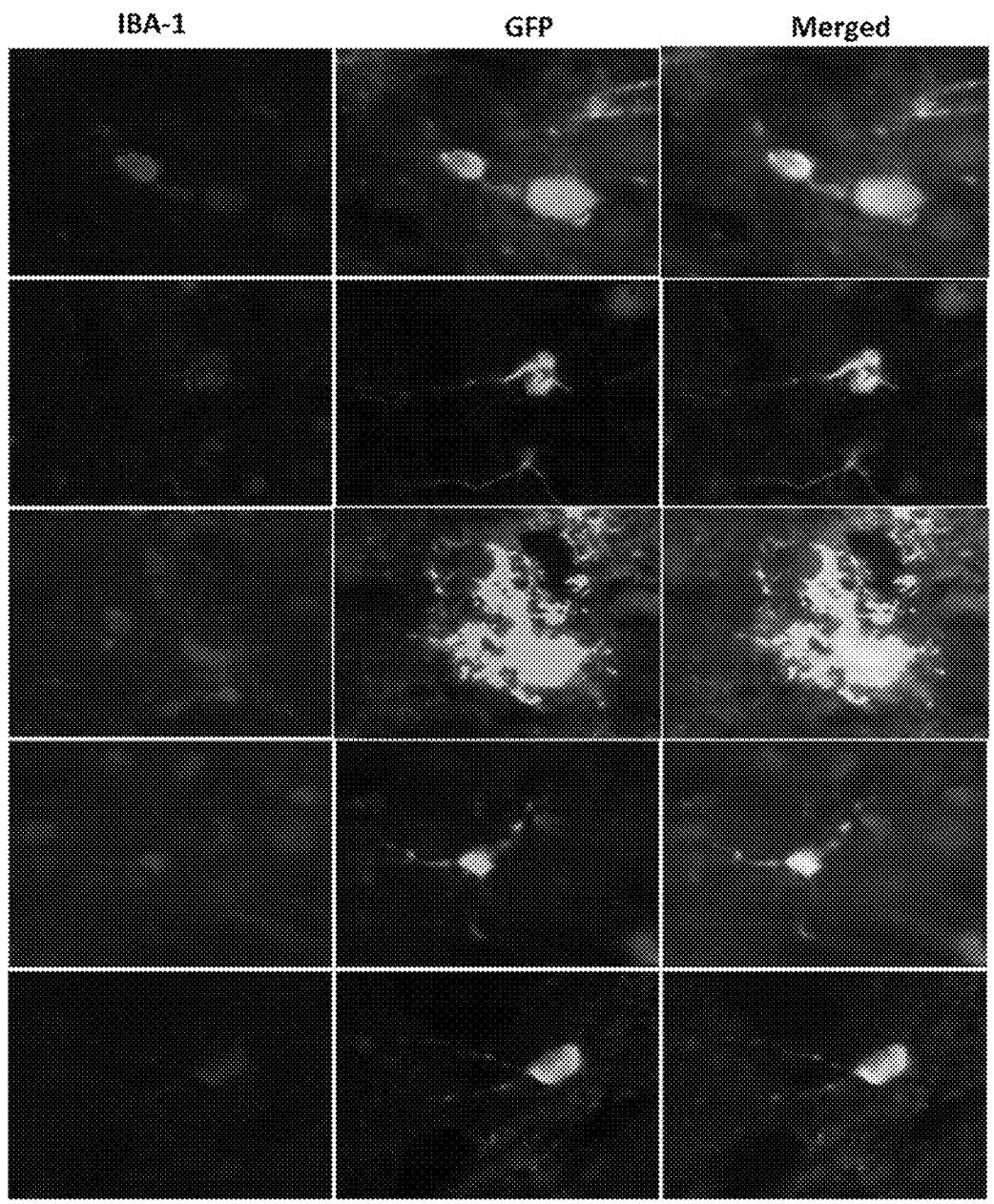
FIG. 5 is a series of photographs showing EGFP expression in murine glial cells in mice injected with wild-type (WT) or mutant AAV6 vectors.

The transduction efficiency of the AAV6 Y705F+Y731F+T492V was significantly higher than the wild-type vector in glial cells in brain tissue (FIG. 5).

Transduction Efficiency of Y705+731F+T492V scAAV6 Vectors in Neurons and Astrocytes in Injected Brains in Mice In Vivo Mice brains were harvested two weeks post injection of $1 \times 10^{10}$ vgs of WT and mutant-AAV6 vectors expressing EGFP. Neurons and astrocytes were identified by cell-specific morphology. Microglia/macrophage-specific marker anti-IBA antibodies were used.

Figure 6:
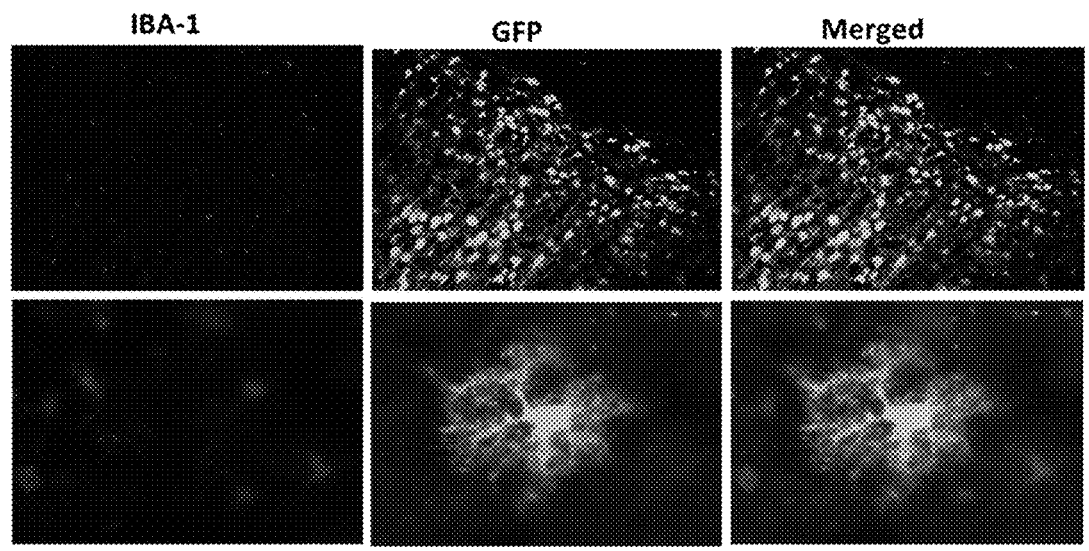
FIG. 6 is a series of photographs showing EGFP expression in neurons and astrocytes in brains from mice injected with mutant AAV6 Y705+731F+T492V vectors.

The AAV6 Y705F+Y731F+T492V was able to transduce neuronal and astrocyte cells in brain tissue (FIG. 6).

Transduction Efficiency of WT and Various Mutant AAV Serotype Vectors in Human Airway Epithelial Cells In Vitro Human normal airway epithelial [4011] cells were infected with WT and mutant AAV1, 2, 5, 6 vectors expressing EGFP at an MOI $2 \times 10^3$ vg/cell. EGFP expression analysis was performed 48 hours post-infection by fluorescent microscopy. Transgene expression was assessed as the total area of green fluorescence (pixel2) per visual field (mean±SD).

Figure 7:
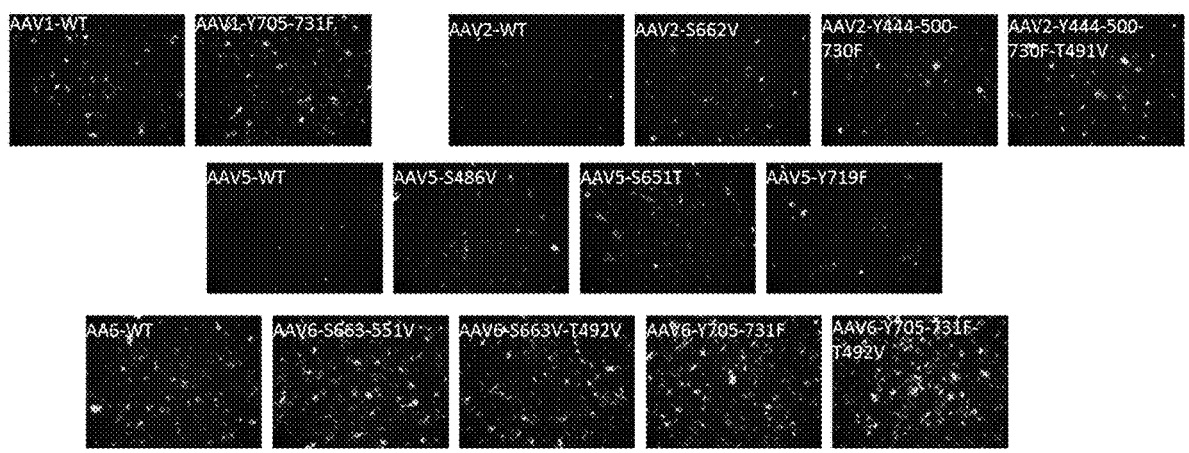
FIG. 7 is a series of photographs and a graph showing EGFP expression in human airway epithelial cells transduced with wild-type (WT) or mutant AAV1, AAV2, AAV5, or AAV6 vectors.

The transduction efficiency of the AAV6 Y705F+Y731F+T492V was significantly higher than the wild-type vector of several serotypes (AAV1, AAV2, AAV5, and AAV6) in human airway epithelial cells (FIG. 7). Double and triple mutants of AAV5 (such as AAV5 triple mutant (Y436F+Y693F+Y719F)), were found to have improved properties compared to the wild-type AAV5 vector (data not shown).

Transduction Efficiency of WT and Various Mutant AAV2 and AAV6 Serotype Vectors in Primary Human Monocyte-Derived Dendritic Cells In Vitro WT and mutant AAV2 and AAV6 vectors carrying a nucleic acid encoding EGFP were produced using standard methods and efficiency of each vector was evaluated in vitro.

Leukapheresis-derived peripheral blood mononuclear cells (PBMCs) were differentiated to dendritic cells (DCs) in the presence of recombinant human IL-4 (500 U/mL) and GM-CSF (800 U/mL). EGFP expression analysis was performed at 48 hours post-infection following transduction at an MOI of $2 \times 10^3$ vgs/cell. Transgene expression was assessed as the total area of green fluorescence (pixel$^2$) per visual field (mean±SD).

Figure 8A:
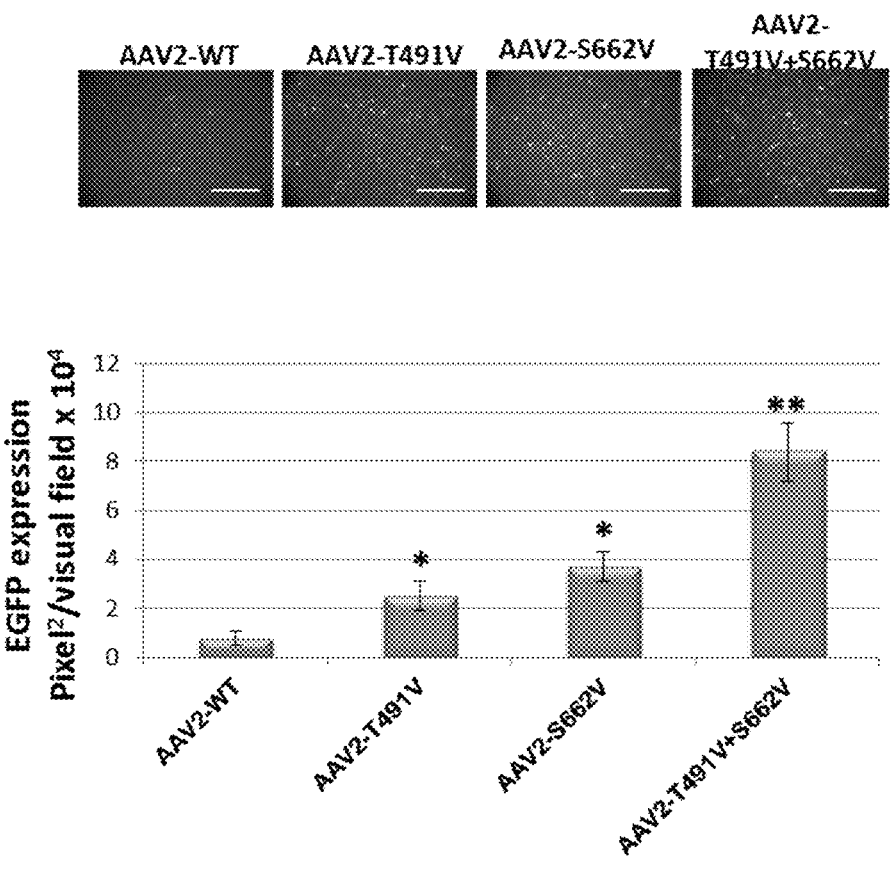
FIG. 8A is a series of photographs and a graph showing EGFP expression in primary human monocyte-derived dendritic cells transduced with wild-type (WT) or mutant AAV2 vectors.
Figure 8B:
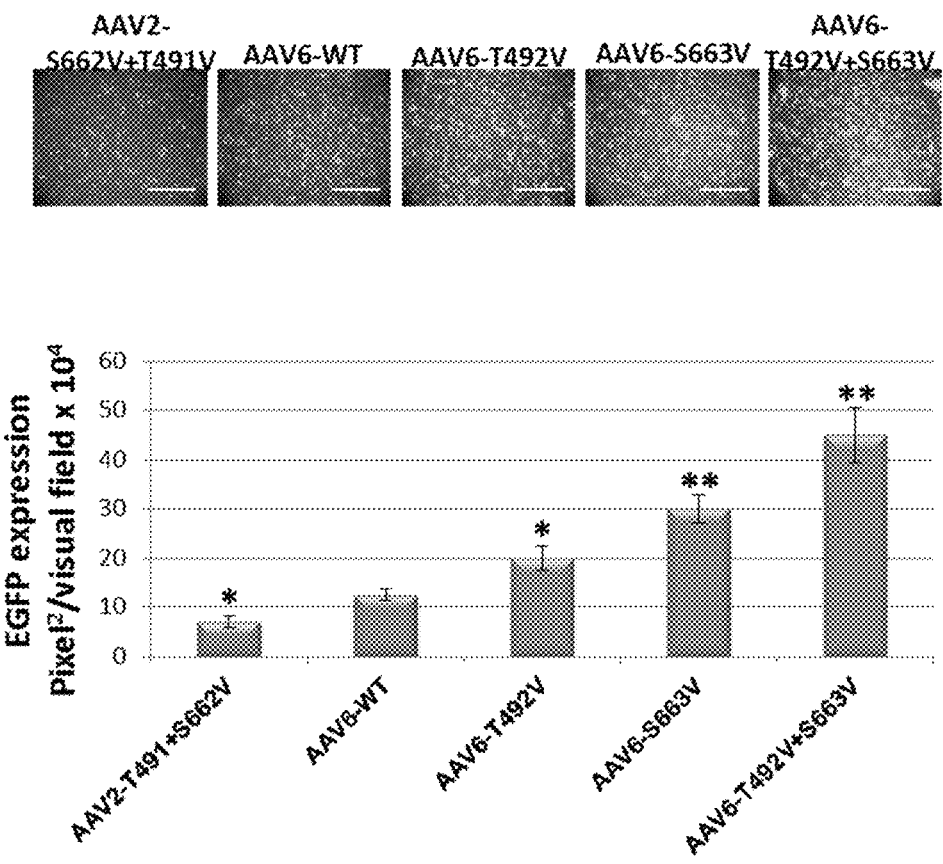
FIG. 8B is a series of photographs and a graph showing EGFP expression in primary human monocyte-derived dendritic cells transduced with wild-type (WT) AAV6 or mutant AAV2 or AAV6 vectors.

The transduction efficiency of the AAV6 Y705F+Y731F+T492V was significantly higher than the wild-type vector of several serotypes (AAV2 and AAV6) in primary human monocyte-derived dendritic cells (FIGS. 8A and 8B).

Other Embodiments

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present disclosure, and without departing from the spirit and scope thereof, can make various changes and modifications of the disclosure to adapt it to various usages and conditions. Thus, other embodiments are also within the claims.

EQUIVALENTS

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

All definitions, as defined and used herein, should be understood to control over dictionary definitions, definitions in documents incorporated by reference, and/or ordinary meanings of the defined terms.

All references, patents and patent applications disclosed herein are incorporated by reference with respect to the subject matter for which each is cited, which in some cases may encompass the entirety of the document.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is claimed is:

1. A modified adeno-associated virus (AAV) capsid protein, wherein a VP3 region of the modified AAV capsid protein comprises a replacement of tyrosine residues with non-tyrosine residues at positions corresponding to:
Y436, Y693, and Y719 of a wild-type AAV5 capsid protein having the sequence of SEQ ID NO: 2.

2. The modified AAV capsid protein of claim 1, wherein the modified AAV capsid protein is a modified AAV5 capsid protein and the modified AAV5 capsid protein comprises replacement of tyrosine residues with non-tyrosine residues at each of the positions corresponding to Y436, Y693, and Y719 of a wild-type AAV5 capsid protein having the sequence of SEQ ID NO: 2.

3. The modified capsid protein of claim 1, wherein the non-tyrosine residues are phenylalanine.

4. A nucleic acid molecule encoding the modified capsid protein of claim 1.

5. The nucleic acid molecule of claim 4, wherein the nucleic acid molecule is a plasmid.

6. A recombinant AAV (rAAV) particle comprising the modified capsid protein of claim 1.

7. A composition comprising a rAAV particle of claim 6 and a pharmaceutically-acceptable carrier.

8. A method, comprising:
contacting a host cell with an rAAV particle comprising the modified AAV capsid protein of claim 1 or a composition comprising the rAAV particle and a pharmaceutically-acceptable carrier.

9. The method of claim 8, wherein the host cell is a hematopoietic stem cell, dendritic cell, a monocyte, a liver cell, a retinal cell or an airway epithelial cell.

10. A method, comprising:
contacting a host cell with an rAAV particle comprising the modified AAV5 capsid protein of claim 2 or a composition comprising the rAAV particle and a pharmaceutically-acceptable carrier.

11. The method of claim 10, wherein the host cell is a retinal or airway epithelial cell.

12. A method, comprising:
contacting a host cell with an rAAV particle comprising the modified AAV capsid protein of claim 3 or a composition comprising the rAAV particle and a pharmaceutically-acceptable carrier.

13. The method of claim 12, wherein the host cell is a hematopoietic stem cell, a dendritic cell, a monocyte, a retinal cell, an airway epithelial cell, a muscle cell, a liver cell, or a microglial cell.

14. A kit comprising the rAAV particle of claim 6.

15. The modified AAV capsid protein of claim 1, wherein the AAV capsid is of serotype AAV1, AAV2, AAV3, AAV4, AAV5, AAV6, AAV7, AAV8, AAV9, AAV10, AAV11, AAV12, or AAV13.

16. The modified AAV capsid protein of claim 3, wherein the modified AAV capsid protein is a modified AAV5 capsid protein and the modified AAV5 capsid protein comprises replacement of tyrosine residues with non-tyrosine residues at each of the positions corresponding to Y436, Y693, and Y719 of a wild-type AAV5 capsid protein having the sequence of SEQ ID NO: 2.

17. The recombinant AAV particle of claim 6, wherein the AAV capsid is of serotype AAV1, AAV2, AAV3, AAV4, AAV5, AAV6, AAV7, AAV8, AAV9, AAV10, AAV11, AAV12, or AAV13.

* * * * *

SEQUENCE LISTING

```
<160> NUMBER OF SEQ ID NOS: 6

<210> SEQ ID NO 1
<211> LENGTH: 736
<212> TYPE: PRT
<213> ORGANISM: Unknown
<220> FEATURE:
<223> OTHER INFORMATION: Adeno-associated virus serotype 1

<400> SEQUENCE: 1

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60
```

-continued

```
Val Asn Ala Ala Asp Ala Ala Leu Glu His Asp Lys Ala Tyr Asp
 65                  70                  75                  80

Gln Gln Leu Lys Ala Gly Asp Asn Pro Tyr Leu Arg Tyr Asn His Ala
                 85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Gly Ala Lys Thr Ala Pro Gly Lys Lys Arg
130                 135                 140

Pro Val Glu Gln Ser Pro Gln Glu Pro Asp Ser Ser Ser Gly Ile Gly
145                 150                 155                 160

Lys Thr Gly Gln Gln Pro Ala Lys Lys Arg Leu Asn Phe Gly Gln Thr
                165                 170                 175

Gly Asp Ser Glu Ser Val Pro Asp Pro Gln Pro Leu Gly Glu Pro Pro
            180                 185                 190

Ala Thr Pro Ala Ala Val Gly Pro Thr Thr Met Ala Ser Gly Gly Gly
        195                 200                 205

Ala Pro Met Ala Asp Asn Asn Glu Gly Ala Asp Gly Val Gly Asn Ala
210                 215                 220

Ser Gly Asn Trp His Cys Asp Ser Thr Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Ser Ala Ser Thr Gly Ala Ser Asn Asp Asn His
            260                 265                 270

Tyr Phe Gly Tyr Ser Thr Pro Trp Gly Tyr Phe Asp Phe Asn Arg Phe
        275                 280                 285

His Cys His Phe Ser Pro Arg Asp Trp Gln Arg Leu Ile Asn Asn Asn
    290                 295                 300

Trp Gly Phe Arg Pro Lys Arg Leu Asn Phe Lys Leu Phe Asn Ile Gln
305                 310                 315                 320

Val Lys Glu Val Thr Thr Asn Asp Gly Val Thr Thr Ile Ala Asn Asn
                325                 330                 335

Leu Thr Ser Thr Val Gln Val Phe Ser Asp Ser Glu Tyr Gln Leu Pro
            340                 345                 350

Tyr Val Leu Gly Ser Ala His Gln Gly Cys Leu Pro Pro Phe Pro Ala
        355                 360                 365

Asp Val Phe Met Ile Pro Gln Tyr Gly Tyr Leu Thr Leu Asn Asn Gly
    370                 375                 380

Ser Gln Ala Val Gly Arg Ser Ser Phe Tyr Cys Leu Glu Tyr Phe Pro
385                 390                 395                 400

Ser Gln Met Leu Arg Thr Gly Asn Asn Phe Thr Phe Ser Tyr Thr Phe
                405                 410                 415

Glu Glu Val Pro Phe His Ser Ser Tyr Ala His Ser Gln Ser Leu Asp
            420                 425                 430

Arg Leu Met Asn Pro Leu Ile Asp Gln Tyr Leu Tyr Tyr Leu Asn Arg
        435                 440                 445

Thr Gln Asn Gln Ser Gly Ser Ala Gln Asn Lys Asp Leu Leu Phe Ser
    450                 455                 460

Arg Gly Ser Pro Ala Gly Met Ser Val Gln Pro Lys Asn Trp Leu Pro
465                 470                 475                 480
```

```
Gly Pro Cys Tyr Arg Gln Gln Arg Val Ser Lys Thr Lys Thr Asp Asn
                485                 490                 495
Asn Asn Ser Asn Phe Thr Trp Thr Gly Ala Ser Lys Tyr Asn Leu Asn
            500                 505                 510
Gly Arg Glu Ser Ile Ile Asn Pro Gly Thr Ala Met Ala Ser His Lys
        515                 520                 525
Asp Asp Glu Asp Lys Phe Phe Pro Met Ser Gly Val Met Ile Phe Gly
    530                 535                 540
Lys Glu Ser Ala Gly Ala Ser Asn Thr Ala Leu Asp Asn Val Met Ile
545                 550                 555                 560
Thr Asp Glu Glu Glu Ile Lys Ala Thr Asn Pro Val Ala Thr Glu Arg
                565                 570                 575
Phe Gly Thr Val Ala Val Asn Phe Gln Ser Ser Ser Thr Asp Pro Ala
            580                 585                 590
Thr Gly Asp Val His Ala Met Gly Ala Leu Pro Gly Met Val Trp Gln
        595                 600                 605
Asp Arg Asp Val Tyr Leu Gln Gly Pro Ile Trp Ala Lys Ile Pro His
    610                 615                 620
Thr Asp Gly His Phe His Pro Ser Pro Leu Met Gly Gly Phe Gly Leu
625                 630                 635                 640
Lys Asn Pro Pro Pro Gln Ile Leu Ile Lys Asn Thr Pro Val Pro Ala
                645                 650                 655
Asn Pro Pro Ala Glu Phe Ser Ala Thr Lys Phe Ala Ser Phe Ile Thr
            660                 665                 670
Gln Tyr Ser Thr Gly Gln Val Ser Val Glu Ile Glu Trp Glu Leu Gln
        675                 680                 685
Lys Glu Asn Ser Lys Arg Trp Asn Pro Glu Val Gln Tyr Thr Ser Asn
    690                 695                 700
Tyr Ala Lys Ser Ala Asn Val Asp Phe Thr Val Asp Asn Asn Gly Leu
705                 710                 715                 720
Tyr Thr Glu Pro Arg Pro Ile Gly Thr Arg Tyr Leu Thr Arg Pro Leu
                725                 730                 735

<210> SEQ ID NO 2
<211> LENGTH: 724
<212> TYPE: PRT
<213> ORGANISM: Unknown
<220> FEATURE:
<223> OTHER INFORMATION: Adeno-associated virus serotype 5

<400> SEQUENCE: 2

Met Ser Phe Val Asp His Pro Pro Asp Trp Leu Glu Glu Val Gly Glu
1               5                   10                  15
Gly Leu Arg Glu Phe Leu Gly Leu Glu Ala Gly Pro Pro Lys Pro Lys
            20                  25                  30
Pro Asn Gln Gln His Gln Asp Gln Ala Arg Gly Leu Val Leu Pro Gly
        35                  40                  45
Tyr Asn Tyr Leu Gly Pro Gly Asn Gly Leu Asp Arg Gly Glu Pro Val
    50                  55                  60
Asn Arg Ala Asp Glu Val Ala Arg Glu His Asp Ile Ser Tyr Asn Glu
65                  70                  75                  80
Gln Leu Glu Ala Gly Asp Asn Pro Tyr Leu Lys Tyr Asn His Ala Asp
                85                  90                  95
Ala Glu Phe Gln Glu Lys Leu Ala Asp Asp Thr Ser Phe Gly Gly Asn
            100                 105                 110
```

-continued

Leu Gly Lys Ala Val Phe Gln Ala Lys Lys Arg Val Leu Glu Pro Phe
        115                 120                 125

Gly Leu Val Glu Glu Gly Ala Lys Thr Ala Pro Thr Gly Lys Arg Ile
    130                 135                 140

Asp Asp His Phe Pro Lys Arg Lys Ala Arg Thr Glu Glu Asp Ser
145                 150                 155                 160

Lys Pro Ser Thr Ser Ser Asp Ala Glu Ala Gly Pro Ser Gly Ser Gln
                165                 170                 175

Gln Leu Gln Ile Pro Ala Gln Pro Ala Ser Ser Leu Gly Ala Asp Thr
            180                 185                 190

Met Ser Ala Gly Gly Gly Pro Leu Gly Asp Asn Asn Gln Gly Ala
        195                 200                 205

Asp Gly Val Gly Asn Ala Ser Gly Asp Trp His Cys Asp Ser Thr Trp
210                 215                 220

Met Gly Asp Arg Val Val Thr Lys Ser Thr Arg Thr Trp Val Leu Pro
225                 230                 235                 240

Ser Tyr Asn Asn His Gln Tyr Arg Glu Ile Lys Ser Gly Ser Val Asp
                245                 250                 255

Gly Ser Asn Ala Asn Ala Tyr Phe Gly Tyr Ser Thr Pro Trp Gly Tyr
        260                 265                 270

Phe Asp Phe Asn Arg Phe His Ser His Trp Ser Pro Arg Asp Trp Gln
    275                 280                 285

Arg Leu Ile Asn Asn Tyr Trp Gly Phe Arg Pro Arg Ser Leu Arg Val
        290                 295                 300

Lys Ile Phe Asn Ile Gln Val Lys Glu Val Thr Val Gln Asp Ser Thr
305                 310                 315                 320

Thr Thr Ile Ala Asn Asn Leu Thr Ser Thr Val Gln Val Phe Thr Asp
                325                 330                 335

Asp Asp Tyr Gln Leu Pro Tyr Val Val Gly Asn Gly Thr Glu Gly Cys
        340                 345                 350

Leu Pro Ala Phe Pro Pro Gln Val Phe Thr Leu Pro Gln Tyr Gly Tyr
    355                 360                 365

Ala Thr Leu Asn Arg Asp Asn Thr Glu Asn Pro Thr Glu Arg Ser Ser
370                 375                 380

Phe Phe Cys Leu Glu Tyr Phe Pro Ser Lys Met Leu Arg Thr Gly Asn
385                 390                 395                 400

Asn Phe Glu Phe Thr Tyr Asn Phe Glu Glu Val Pro Phe His Ser Ser
                405                 410                 415

Phe Ala Pro Ser Gln Asn Leu Phe Lys Leu Ala Asn Pro Leu Val Asp
            420                 425                 430

Gln Tyr Leu Tyr Arg Phe Val Ser Thr Asn Asn Thr Gly Gly Val Gln
    435                 440                 445

Phe Asn Lys Asn Leu Ala Gly Arg Tyr Ala Asn Thr Tyr Lys Asn Trp
450                 455                 460

Phe Pro Gly Pro Met Gly Arg Thr Gln Gly Trp Asn Leu Gly Ser Gly
465                 470                 475                 480

Val Asn Arg Ala Ser Val Ser Ala Phe Ala Thr Thr Asn Arg Met Glu
                485                 490                 495

Leu Glu Gly Ala Ser Tyr Gln Val Pro Pro Gln Pro Asn Gly Met Thr
            500                 505                 510

Asn Asn Leu Gln Gly Ser Asn Thr Tyr Ala Leu Glu Asn Thr Met Ile
        515                 520                 525

Phe Asn Ser Gln Pro Ala Asn Pro Gly Thr Thr Ala Thr Tyr Leu Glu

```
                530             535             540
Gly Asn Met Leu Ile Thr Ser Glu Ser Glu Thr Gln Pro Val Asn Arg
545                 550             555                 560

Val Ala Tyr Asn Val Gly Gly Gln Met Ala Thr Asn Asn Gln Ser Ser
                565             570                 575

Thr Thr Ala Pro Ala Thr Gly Thr Tyr Asn Leu Gln Glu Ile Val Pro
                580             585                 590

Gly Ser Val Trp Met Glu Arg Asp Val Tyr Leu Gln Gly Pro Ile Trp
            595             600                 605

Ala Lys Ile Pro Glu Thr Gly Ala His Phe His Pro Ser Pro Ala Met
            610             615             620

Gly Gly Phe Gly Leu Lys His Pro Pro Pro Met Met Leu Ile Lys Asn
625             630             635                 640

Thr Pro Val Pro Gly Asn Ile Thr Ser Phe Ser Asp Val Pro Val Ser
                645             650                 655

Ser Phe Ile Thr Gln Tyr Ser Thr Gly Gln Val Thr Val Glu Met Glu
                660             665             670

Trp Glu Leu Lys Lys Glu Asn Ser Lys Arg Trp Asn Pro Glu Ile Gln
            675             680             685

Tyr Thr Asn Asn Tyr Asn Asp Pro Gln Phe Val Asp Phe Ala Pro Asp
            690             695             700

Ser Thr Gly Glu Tyr Arg Thr Thr Arg Pro Ile Gly Thr Arg Tyr Leu
705             710             715                 720

Thr Arg Pro Leu

<210> SEQ ID NO 3
<211> LENGTH: 736
<212> TYPE: PRT
<213> ORGANISM: Unknown
<220> FEATURE:
<223> OTHER INFORMATION: Adeno-associated virus serotype 6

<400> SEQUENCE: 3

Met Ala Ala Asp Gly Tyr Leu Pro Asp Trp Leu Glu Asp Asn Leu Ser
1               5               10                  15

Glu Gly Ile Arg Glu Trp Trp Asp Leu Lys Pro Gly Ala Pro Lys Pro
            20              25                  30

Lys Ala Asn Gln Gln Lys Gln Asp Asp Gly Arg Gly Leu Val Leu Pro
        35              40                  45

Gly Tyr Lys Tyr Leu Gly Pro Phe Asn Gly Leu Asp Lys Gly Glu Pro
    50              55                  60

Val Asn Ala Ala Asp Ala Ala Ala Leu Glu His Asp Lys Ala Tyr Asp
65              70                  75                  80

Gln Gln Leu Lys Ala Gly Asp Asn Pro Tyr Leu Arg Tyr Asn His Ala
            85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Phe Gly Leu Val Glu Glu Gly Ala Lys Thr Ala Pro Gly Lys Lys Arg
    130                 135                 140

Pro Val Glu Gln Ser Pro Gln Glu Pro Asp Ser Ser Ser Gly Ile Gly
145                 150                 155                 160

Lys Thr Gly Gln Gln Pro Ala Lys Lys Arg Leu Asn Phe Gly Gln Thr
            165                 170                 175
```

-continued

```
Gly Asp Ser Glu Ser Val Pro Asp Pro Gln Pro Leu Gly Glu Pro Pro
            180                 185                 190

Ala Thr Pro Ala Ala Val Gly Pro Thr Thr Met Ala Ser Gly Gly Gly
        195                 200                 205

Ala Pro Met Ala Asp Asn Asn Glu Gly Ala Asp Gly Val Gly Asn Ala
    210                 215                 220

Ser Gly Asn Trp His Cys Asp Ser Thr Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Ser Ala Ser Thr Gly Ala Ser Asn Asp Asn His
            260                 265                 270

Tyr Phe Gly Tyr Ser Thr Pro Trp Gly Tyr Phe Asp Phe Asn Arg Phe
        275                 280                 285

His Cys His Phe Ser Pro Arg Asp Trp Gln Arg Leu Ile Asn Asn Asn
    290                 295                 300

Trp Gly Phe Arg Pro Lys Arg Leu Asn Phe Lys Leu Phe Asn Ile Gln
305                 310                 315                 320

Val Lys Glu Val Thr Thr Asn Asp Gly Val Thr Thr Ile Ala Asn Asn
                325                 330                 335

Leu Thr Ser Thr Val Gln Val Phe Ser Asp Ser Glu Tyr Gln Leu Pro
            340                 345                 350

Tyr Val Leu Gly Ser Ala His Gln Gly Cys Leu Pro Pro Phe Pro Ala
        355                 360                 365

Asp Val Phe Met Ile Pro Gln Tyr Gly Tyr Leu Thr Leu Asn Asn Gly
    370                 375                 380

Ser Gln Ala Val Gly Arg Ser Ser Phe Tyr Cys Leu Glu Tyr Phe Pro
385                 390                 395                 400

Ser Gln Met Leu Arg Thr Gly Asn Asn Phe Thr Phe Ser Tyr Thr Phe
                405                 410                 415

Glu Asp Val Pro Phe His Ser Ser Tyr Ala His Ser Gln Ser Leu Asp
            420                 425                 430

Arg Leu Met Asn Pro Leu Ile Asp Gln Tyr Leu Tyr Phe Leu Asn Arg
        435                 440                 445

Thr Gln Asn Gln Ser Gly Ser Ala Gln Asn Lys Asp Leu Leu Phe Ser
    450                 455                 460

Arg Gly Ser Pro Ala Gly Met Ser Val Gln Pro Lys Asn Trp Leu Pro
465                 470                 475                 480

Gly Pro Cys Tyr Arg Gln Gln Arg Val Ser Lys Thr Lys Thr Asp Asn
                485                 490                 495

Asn Asn Ser Asn Phe Thr Trp Thr Gly Ala Ser Lys Tyr Asn Leu Asn
            500                 505                 510

Gly Arg Glu Ser Ile Ile Asn Pro Gly Thr Ala Met Ala Ser His Lys
        515                 520                 525

Asp Asp Lys Asp Lys Phe Phe Pro Met Ser Gly Val Met Ile Phe Gly
    530                 535                 540

Lys Glu Ser Ala Gly Ala Ser Asn Thr Ala Leu Asp Asn Val Met Ile
545                 550                 555                 560

Thr Asp Glu Glu Glu Ile Lys Ala Thr Asn Pro Val Ala Thr Glu Arg
                565                 570                 575

Phe Gly Thr Val Ala Val Asn Leu Gln Ser Ser Ser Thr Asp Pro Ala
            580                 585                 590
```

```
Thr Gly Asp Val His Val Met Gly Ala Leu Pro Gly Met Val Trp Gln
        595                 600                 605

Asp Arg Asp Val Tyr Leu Gln Gly Pro Ile Trp Ala Lys Ile Pro His
    610                 615                 620

Thr Asp Gly His Phe His Pro Ser Pro Leu Met Gly Gly Phe Gly Leu
625                 630                 635                 640

Lys His Pro Pro Gln Ile Leu Ile Lys Asn Thr Pro Val Pro Ala
                645                 650                 655

Asn Pro Pro Ala Glu Phe Ser Ala Thr Lys Phe Ala Ser Phe Ile Thr
            660                 665                 670

Gln Tyr Ser Thr Gly Gln Val Ser Val Glu Ile Glu Trp Glu Leu Gln
        675                 680                 685

Lys Glu Asn Ser Lys Arg Trp Asn Pro Glu Val Gln Tyr Thr Ser Asn
    690                 695                 700

Tyr Ala Lys Ser Ala Asn Val Asp Phe Thr Val Asp Asn Asn Gly Leu
705                 710                 715                 720

Tyr Thr Glu Pro Arg Pro Ile Gly Thr Arg Tyr Leu Thr Arg Pro Leu
                725                 730                 735

<210> SEQ ID NO 4
<211> LENGTH: 2211
<212> TYPE: DNA
<213> ORGANISM: Artificial Sequence
<220> FEATURE:
<223> OTHER INFORMATION: Synthetic Polynucleotide

<400> SEQUENCE: 4
atggctgccg atggttatct tccagattgg ctcgaggaca acctctctga gggcattcgc       60
gagtggtggg acttgaaacc tggagccccg aagcccaaag ccaaccagca aaagcaggac      120
gacggccggg gtctggtgct tcctggctac aagtacctcg acccttcaa cggactcgac       180 aaggggagc ccgtcaacgc ggcggacgca gcggccctcg agcacgacaa ggcctacgac       240
cagcagctca aagcgggtga caatccgtac ctgcggtata ccacgccga cgccgagttt       300 caggagcgtc tgcaagaaga tacgtctttt gggggcaacc tcgggcgagc agtcttccag      360
gccaagaagc gggttctcga acctctcggt ctggttgagg aaggcgctaa gacggctcct      420
ggaaagaaac gtccggtaga gcagtcgcca caagagccag actcctcctc gggcatcggc      480
aagacaggcc agcagcccgc taaaagaga ctcaattttg gtcagactgg cgactcagag       540
tcagtccccg atccacaacc tctcggagaa cctccagcaa ccccgctgc tgtgggacct       600 actacaatgg cttcaggcgg tggcgcacca atggcagaca taacgaagg cgccgacgga       660 gtgggtaatg cctcaggaaa ttggcattgc gattccacat ggctgggcga cagagtcatc       720
accaccagca cccgcacctg gccttgccc acctacaata accacctcta caagcaaatc       780
tccagtgctt caacgggggc cagcaacgac aaccactact cggctacag caccccctgg       840 gggtattttg atttcaacag attccactgc cacttttcac cacgtgactg gcagcgactc       900
atcaacaaca attggggatt ccggcccaag agactcaact tcaaactctt caacatccaa       960
gtcaaggagg tcacgacgaa tgatggcgtc acaaccatcg ctaataacct taccagcacg      1020
gttcaagtct ctcggactc ggagtaccag cttccgtacg tcctcggctc tgcgcaccag      1080
ggctgcctcc ctcgttccc ggcggacgtg ttcatgattc cgcaatacgg ctacctgacg      1140
ctcaacaatg cagccaagc cgtgggacgt tcatcctttt actgcctgga atatttccct      1200
tctcagatgc tgagaacggg caacaacttt accttcagct acaccttga ggaagtgcct      1260
```

| | | |
|---|---|---|
| ttccacagca gctacgcgca cagccagagc ctggaccggc tgatgaatcc tctcatcgac | 1320 | |
| caatacctgt attacctgaa cagaactcaa aatcagtccg gaagtgccca aaacaaggac | 1380 | |
| ttgctgttta gccgtgggtc tccagctggc atgtctgttc agcccaaaaa ctggctacct | 1440 | |
| ggaccctgtt atcggcagca gcgcgttttct aaagtaaaaa cagacaacaa caacagcaat | 1500 | |
| tttacctgga ctggtgcttc aaaatataac ctcaatgggc gtgaatccat catcaaccct | 1560 | |
| ggcactgcta tggcctcaca caaagacgac gaagacaagt tctttcccat gagcggtgtc | 1620 | |
| atgattttg gaaagagag cgccggagct tcaaacactg cattgacaa tgtcatgatt | 1680 | |
| acagacgaag aggaaattaa agccactaac cctgtggcca ccgaaagatt tgggaccgtg | 1740 | |
| gcagtcaatt tccagagcag cagcacagac cctgcgaccg gagatgtgca tgctatggga | 1800 | |
| gcattacctg gcatggtgtg gcaagataga acgtgtacc tgcagggtcc catttgggcc | 1860 | |
| aaaattcctc acacagatgg acactttcac ccgtctcctc ttatgggcgg ctttggactc | 1920 | |
| aagaacccgc ctcctcagat cctcatcaaa aacacgcctg ttcctgcgaa tcctccggcg | 1980 | |
| gagttttcag ctacaaagtt tgcttcattc atcacccaat actccacagg acaagtgagt | 2040 | |
| gtggaaattg aatgggagct gcagaaagaa aacagcaagc gctggaatcc gaagtgcag | 2100 | |
| tacacatcca attttgcaaa atctgccaat gttgatttta ctgtggacaa caatggactt | 2160 | |
| tatactgagc ctcgccccat tggcacgcgt ttccttaccc gtcccctgta a | 2211 | |

<210> SEQ ID NO 5
<211> LENGTH: 2175
<212> TYPE: DNA
<213> ORGANISM: Artificial Sequence
<220> FEATURE:
<223> OTHER INFORMATION: Synthetic Polynucleotide

<400> SEQUENCE: 5

| | | |
|---|---|---|
| atgtcttttg ttgatcaccc tccagattgg ttggaagaag ttggtgaagg tcttcgcgag | 60 | |
| tttttgggcc ttgaagcggg cccaccgaaa ccaaaaccca atcagcagca tcaagatcaa | 120 | |
| gcccgtggtc ttgtgctgcc tggttataac tatctcggac ccggaaacgg tctcgatcga | 180 | |
| ggagagcctg tcaacagggc agacgaggtc gcgcgagagc acgacatctc gtacaacgag | 240 | |
| cagcttgagg cgggagacaa ccccctacctc aagtacaacc acgcggacgc cgagtttcag | 300 | |
| gagaagctcg ccgacgacac atccttcggg ggaaacctcg gaaaggcagt cttttcaggcc | 360 | |
| aagaaaaggg ttctcgaacc ttttggcctg gttgagagg gtgctaagac ggcccctacc | 420 | |
| ggaaagcgga tagacgacca cttttccaaaa agaaagaagg ctcggaccga agaggactcc | 480 | |
| aagccttcca cctcgtcaga cgccgaagct ggacccagcg atcccagca gctgcaaatc | 540 | |
| ccagcccaac cagcctcaag tttgggagct gatacaatgt ctgcgggagg tggcggccca | 600 | |
| ttgggcgaca ataccaaagg tgccgatgga gtgggcaatg cctcgggaga ttggcattgc | 660 | |
| gattccacgt ggatggggga cagagtcgtc accaagtcca cccgaacctg ggtgctgccc | 720 | |
| agctacaaca accaccagta ccgagagatc aaaagcggct ccgtcgacgg aagcaacgcc | 780 | |
| aacgcgttct ttggatacag cacccctgg gggtactttg actttaaccg cttccacagc | 840 | |
| cactggagcc cccgagactg gcaaagactc atcaacaact actggggctt cagacccgg | 900 | |
| tccctcagag tcaaaatctt caacattcaa gtcaaagagg tcacggtgca ggactccacc | 960 | |
| accaccatcg ccaacaacct cacctccacc gtccaagtgt ttacggacga cgactaccag | 1020 | |
| ctgccctacg tcgtcggcaa cgggaccgag ggatgcctgc cggccttccc tccgcaggtc | 1080 | |
| tttacgctgc cgcagtacgg ttacgcgacg ctgaaccgcg acaacacaga aaatccaacc | 1140 | |

```
gagaggagca gcttcttctg cctagagtac tttcccagca agatgctgag aacgggcaac    1200
aactttgagt ttacctacaa cttttgaggag gtgcccttcc actccagctt cgctcccagt   1260
cagaacctct tcaagctggc caacccgctg gtggaccagt acttgtaccg cttcgtgagc    1320
acaaataaca ctggcggagt ccagttcaac aagaacctgg ccgggagata cgccaacacc    1380
tacaaaaact ggttcccggg gcccatgggc cgaacccagg gctggaacct gggctccggg    1440
gtcaaccgcg ccagtgtcag cgccttcgcc acgaccaata ggatggagct cgagggcgcg    1500
agttaccagg tgcccccgca gccgaacggc atgaccaaca acctccaggg cagcaacacc    1560
tatgccctgg agaacactat gatcttcaac agccagccgg cgaacccggg caccaccgcc    1620
acgtacctcg agggcaacat gctcatcacc agcgagagcg agacgcagcc ggtgaaccgc    1680
gtggcgtaca acgtcggcgg gcagatggcc accaacaacc agagctccac cactgccccc    1740
gcgaccggca cgtacaacct ccaggaaatc gtgcccggca gcgtgtggat ggagagggac    1800
gtgtacctcc aaggacccat ctgggccaag atcccagaga cggggcgca ctttcacccc     1860 tctccggcca tgggcggatt cggactcaaa cacccaccgc ccatgatgct catcaagaac    1920
acgcctgtgc ccggaaatat caccagcttc tcggacgtgc ccgtcagcag cttcatcacc    1980
cagtacagca ccgggcaggt caccgtggag atggagtggg agctcaagaa ggaaaactcc    2040
aagaggtgga acccagagat ccagtacaca aacaactaca cgacccca gtttgtggac      2100 tttgccccgg acagcaccgg ggaatacaga accaccagac ctatcggaac gcgtttcctt    2160
acccgacccc tttaa                                                     2175
```

<210> SEQ ID NO 6
<211> LENGTH: 2211
<212> TYPE: DNA
<213> ORGANISM: Artificial Sequence
<220> FEATURE:
<223> OTHER INFORMATION: Synthetic Polynucleotide

<400> SEQUENCE: 6

```
atggctgccg atggttatct tccagattgg ctcgaggaca acctctctga gggcattcgc     60
gagtggtggg acttgaaacc tggagccccg aaacccaaag ccaaccagca aaagcaggac   120
gacggccggg gtctggtgct tcctggctac aagtacctcg gacccttcaa cggactcgac   180
aagggggagc ccgtcaacgc ggcggatgca gcggccctcg agcacgacaa ggcctacgac   240
cagcagctca aagcgggtga caatccgtac ctgcggtata accacgccga cgccgagttt   300
caggagcgtc tgcaagaaga tacgtctttt ggggcaacc tcgggcgagc agtcttccag    360
gccaagaaga gggttctcga acctttggt ctggttgagg aaggtgctaa gacggctcct    420
ggaaagaaac gtccggtaga gcagtcgcca aagagccag actcctcctc gggcattggc    480
aagacaggcc agcagcccgc taaaaagaga ctcaattttg gtcagactgg cgactcagag   540
tcagtccccg acccacaacc tctcggagaa cctccagcaa ccccgctgc tgtgggacct    600 actacaatgg cttcaggcgg tggcgcacca atggcagaca taacgaagg cgccgacgga    660 gtgggtaatg cctcaggaaa ttggcattgc gattccacat ggctgggcga cagagtcatc    720
accaccagca cccgaacatg ggccttgccc acctataaca accacctcta caagcaaatc    780
tccagtgctt caacggggc cagcaacgac aaccactact cggctacag cacccctgg      840 gggtatttg atttcaacag attccactgc catttctcac cacgtgactg gcagcgactc     900
atcaacaaca attggggatt ccggcccaag agactcaact tcaagctctt caacatccaa    960
```

```
gtcaaggagg tcacgacgaa tgatggcgtc acgaccatcg ctaataacct taccagcacg    1020
gttcaagtct tctcggactc ggagtaccag ttgccgtacg tcctcggctc tgcgcaccag    1080
ggctgcctcc ctccgttccc ggcggacgtg ttcatgattc cgcagtacgg ctacctaacg    1140
ctcaacaatg gcagccaggc agtgggacgg tcatccttt actgcctgga atatttccca    1200
tcgcagatgc tgagaacggg caataacttt accttcagct acaccttcga ggacgtgcct    1260
ttccacagca gctacgcgca cagccagagc ctggaccggc tgatgaatcc tctcatcgac    1320
cagtacctgt attacctgaa cagaactcag aatcagtccg gaagtgccca aaacaaggac    1380
ttgctgttta gccggggggtc tccagctggc atgtctgttc agcccaaaaa ctggctacct    1440
ggaccctgtt accggcagca gcgcgtttct aaagtaaaaa cagacaacaa caacagcaac    1500
tttacctgga ctggtgcttc aaaatataac cttaatgggc gtgaatctat aatcaaccct    1560
ggcactgcta tggcctcaca caaagacgac aaagacaagt tctttcccat gagcggtgtc    1620 atgattttg gaaaggagag cgccggagct tcaaacactg cattggacaa tgtcatgatc    1680
acagacgaag aggaaatcaa agccactaac cccgtggcca ccgaaagatt tgggactgtg    1740
gcagtcaatc tccagagcag cagcacagac cctgcgaccg gagatgtgca tgttatggga    1800
gccttacctg gaatggtgtg gcaagacaga gacgtatacc tgcagggtcc tatttgggcc    1860
aaaattcctc acacggatgg acactttcac ccgtctcctc tcatgggcgg ctttggactt    1920
aagcacccgc ctcctcagat cctcatcaaa aacacgcctg ttcctgcgaa tcctccggca    1980
gagttttcgg ctacaaagtt tgcttcattc atcacccagt attccacagg acaagtgagc    2040
gtggagattg aatgggagct gcagaaagaa aacagcaaac gctggaatcc cgaagtgcag    2100
tatacatcta actttgccaa atctgccaac gttgatttca ctgtggacaa caatggactt    2160
tatactgagc ctcgccccat tggcacacgt ttcctcaccc gtcccctgta a             2211
```